United States Patent
Beard et al.

(10) Patent No.: US 8,580,817 B2
(45) Date of Patent: Nov. 12, 2013

(54) 1-(1-OXO-1,2,3,4-TETRAHYDROISO-QUINOLIN-7-YL)UREA DERIVATIVES AS N-FORMYL PEPTIDE RECEPTOR LIKE-1 (FPRL-1) RECEPTOR MODULATORS

(75) Inventors: Richard L. Beard, NewportBeach, CA (US); John E. Donello, Dana Point, CA (US); Tien T. Duong, Rancho Santa Margarita, CA (US); Michael E. Garst, Newport Beach, CA (US); Veena Viswanath, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 13 days.

(21) Appl. No.: 13/370,472

(22) Filed: Feb. 10, 2012

(65) Prior Publication Data

US 2012/0208842 A1 Aug. 16, 2012

Related U.S. Application Data

(60) Provisional application No. 61/441,824, filed on Feb. 11, 2011.

(51) Int. Cl.
*C07D 217/24* (2006.01)
*C07D 401/02* (2006.01)
*A61K 31/47* (2006.01)

(52) U.S. Cl.
USPC .......................................... 514/309; 546/141

(58) Field of Classification Search
None
See application file for complete search history.

(56) References Cited

U.S. PATENT DOCUMENTS 7,931,909 B2 4/2011 Hughes et al.
2002/0016460 A1 2/2002 Snow

FOREIGN PATENT DOCUMENTS

WO 2005-047899 5/2005
WO 2009-051670 4/2009

OTHER PUBLICATIONS

Roland Burli, 2006, Potent hFPRL1 (ALXR) Agonists as Potential Anti-Inflammatory Agents, Bioorganic & Medicinal Chemistry Letters, 16, 3713-3718.
"Rules for the Nomenclature of Organic Chemistry, Section E: Stereochemisty," Pure Applied Chemistry, 1976, vol. 45, pp. 11-30.
Ni, Yidong, et al., "New approach for preparation of 2,3,7-trisubstituted 3,4-dihydroisoquinolinone libraries on solid phase," 2000, Molecular Diversity, 5, pp. 153-161.
Stahl, P. Heinrich, et al., "New approach for preparaton of 2,3,7-trisubstituted 3,4-dihydroisoquinolinone libraries on solid phase," Handbook of Pharmaceutical Salts helvetica Chimica Acta, 2002, pp. 329-345.
Perretti, Mauro, et al., "Therapeutic anti-inflammatory potential of formyl-peptide receptor agonists," Pharmacology & Therapeutics, 2010, 127, pp. 175-188.

*Primary Examiner* — Zinna Northington Davis
(74) *Attorney, Agent, or Firm* — Doina G. Ene

(57) ABSTRACT

The present invention relates to novel 1-(1-Oxo-1,2,3,4-tetrahydroisoquinolin-7-yl)urea derivatives, processes for preparing them, pharmaceutical compositions containing them and their use as pharmaceuticals as modulators of the N-formyl peptide receptor like-1 (FPRL-1) receptor.

13 Claims, No Drawings

1-(1-OXO-1,2,3,4-TETRAHYDROISO-QUINOLIN-7-YL)UREA DERIVATIVES AS N-FORMYL PEPTIDE RECEPTOR LIKE-1 (FPRL-1) RECEPTOR MODULATORS

RELATED APPLICATION

This application claims the benefit of U.S. Provisional Application Ser. No. 61/441,824, filed Feb. 11, 2011, the disclosure of which is hereby incorporated in its entirety herein by reference.

FIELD OF THE INVENTION

The present invention relates to novel 1-(1-Oxo-1,2,3,4-tetrahydroisoquinolin-7-yl)urea derivatives, processes for preparing them, pharmaceutical compositions containing them and their use as pharmaceuticals as modulators of the N-formyl peptide receptor like-1 (FPRL-1) receptor. The invention relates specifically to the use of these compounds and their pharmaceutical compositions to treat disorders associated with the N-formyl peptide receptor like-1 (FPRL-1) receptor modulation.

BACKGROUND OF THE INVENTION

The N-formyl peptide receptor like-1 (FPRL-1) receptor is a G protein-coupled receptor that is expressed on inflammatory cells such as monocytes and neutrophils, as well as T cells and has been shown to play a critical role in leukocyte trafficking during inflammation and human pathology. FPRL-1 is an exceptionally promiscuous receptor that responds to a large array of exogenous and endogenous ligands, including Serum amyloid A (SAA), chemokine variant sCKβ8-1, the neuroprotective peptide humanin, anti-inflammatory eicosanoid lipoxin A4 (LXA4) and glucocotricoid-modulated protein annexin A1. FPRL-1 transduces anti-inflammatory effects of LXA4 in many systems, but it also can mediate the pro-inflammatory signaling cascade of peptides such as SAA. The ability of the receptor to mediate two opposite effects is proposed to be a result of different receptor domains used by different agonists. Parmentier, Marc et al. Cytokine & Growth Factor Reviews 17 (2006) 501-519.

Activation of FPRL-1 by lipoxin A4 or its analogs and by Annexin I protein has been shown to result in anti-inflammatory activity by promoting active resolution of inflammation which involves inhibition of polymorphonuclear neutrophils (PMNs) and eosinophils migration and also stimulate monocyte migration enabling clearance of apoptotic cells from the site of inflammation in a nonphlogistic manner. In addition, FPRL-1 has been shown to inhibit NK cytotoxicity and promote activation of T cells which further contributes to down regulation of tissue damaging inflammatory signals. FPRL-1/LXA4 interaction has been shown to be beneficial in experimental models of ischemia reperfusion, angiogenesis, dermal inflammation, chemotherapy-induced alopecia, ocular inflammation such as endotoxin-induced uveitis, corneal wound healing, re-epithelialization etc. FPRL-1 thus represents an important novel pro-resolutionary molecular target for the development of new therapeutic agents in diseases with excessive inflammatory responses.

SUMMARY OF THE INVENTION

A group of novel compounds which are potent and selective FPRL-1 modulators has now been discovered. As such, the compounds described herein are useful in treating a wide variety of disorders associated with modulation of FPRL-1 receptor. The term "modulator" as used herein, includes but is not limited to: receptor agonist, antagonist, inverse agonist, inverse antagonist, partial agonist, partial antagonist.

This invention describes compounds of Formula I, which have FPRL-1 receptor biological activity. The compounds in accordance with the present invention are thus of use in medicine, for example in the treatment of humans with diseases and conditions that are alleviated by FPRL-1 modulation.

In one aspect, the invention provides a compound having Formula I or a pharmaceutically acceptable salt thereof or stereoisomeric forms thereof, or the geometrical isomers, enantiomers, diastereoisomers, tautomers, zwitterions and pharmaceutically acceptable salts thereof:

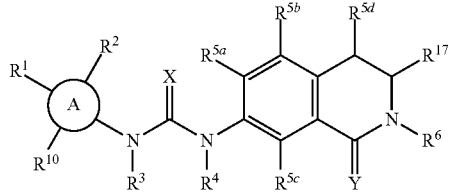

Formula I wherein:

A is $C_{6-10}$ aryl, Heterocyle, $C_{3-8}$ cycloalkyl or $C_{3-8}$ cycloalkenyl;

$R^{17}$ is $C_{1-6}$ alkyl or

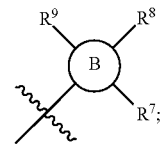

B is $C_{6-10}$ aryl, heterocyle, $C_{3-8}$ cycloalkyl or $C_{3-8}$ cycloalkenyl;

$R^1$ is H, halogen, —S(O)$R^{15}$, —S(O)$_2R^{11}$, nitro, cyano, —OC$_{1-6}$ alkyl, —SC$_{1-6}$ alkyl, —C$_{1-6}$ alkyl, —C$_{2-6}$ alkenyl, —C$_{2-6}$ alkynyl, C(O)$R^{12}$, NR$^{13}R^{14}$, C$_{3-8}$ cycloalkyl or hydroxyl;

$R^2$ is H, halogen, —S(O)$R^{15}$, —S(O)$_2R^{11}$, nitro, cyano, —OC$_{1-6}$ alkyl, —SC$_{1-6}$ alkyl, —C$_{1-6}$ alkyl, —C$_{2-6}$ alkenyl, —C$_{2-6}$ alkynyl, C(O)$R^{12}$, NR$^{13}R^{14}$, C$_{3-8}$ cycloalkyl or hydroxyl;

$R^3$ is H, $C_{1-6}$ alkyl or $C_{3-8}$ cycloalkyl;
$R^4$ is H, $C_{1-6}$ alkyl or $C_{3-8}$ cycloalkyl;
$R^{5a}$ is H, halogen, —S(O)$R^{15}$, —S(O)$_2R^{11}$, nitro, cyano, —OC$_{1-6}$ alkyl, —SC$_{1-6}$ alkyl, —C$_{1-6}$ alkyl, —C$_{2-6}$ alkenyl, —C$_{2-6}$ alkynyl, C(O)$R^{12}$, NR$^{13}R^{14}$, C$_{3-8}$ cycloalkyl or hydroxyl;
$R^{5b}$ is H, halogen, —S(O)$R^{15}$, —S(O)$_2R^{11}$, nitro, cyano, —OC$_{1-6}$ alkyl, —SC$_{1-6}$ alkyl, —C$_{1-6}$ alkyl, —C$_{2-6}$ alkenyl, —C$_{2-6}$ alkynyl, C(O)$R^{12}$, NR$^{13}R^{14}$, C$_{3-8}$ cycloalkyl or hydroxyl;
$R^{5c}$ is H, halogen, —S(O)$R^{15}$, —S(O)$_2R^{11}$, nitro, cyano, —OC$_{1-6}$ alkyl, —SC$_{1-6}$ alkyl, —C$_{1-6}$ alkyl, —C$_{2-6}$ alkenyl, —C$_{2-6}$ alkynyl, C(O)$R^{12}$, NR$^{13}R^{14}$, C$_{3-8}$ cycloalkyl or hydroxyl;
$R^{5d}$ is H, halogen, —S(O)$R^{15}$, —S(O)$_2R^{11}$, nitro, cyano, —OC$_{1-6}$ alkyl, —SC$_{1-6}$ alkyl, —C$_{1-6}$ alkyl, —C$_{2-6}$ alkenyl, —C$_{2-6}$ alkynyl, C(O)$R^{12}$, NR$^{13}R^{14}$, C$_{3-8}$ cycloalkyl or hydroxyl;

$R^6$ is H, —S(O)$_2$R$^{11}$, —C$_{1-6}$ alkyl, —(CH$_2$)$_n$ NR$^{13}$R$^{14}$, —(CH$_2$)$_m$ heterocycle, C(O)R$^{12}$, NR$^{13}$R$^{14}$, C$_{3-8}$ cycloalkyl, C$_{6-10}$ aryl, or heterocycle;

$R^7$ is H, halogen, —S(O)R$^{15}$, —S(O)$_2$R$^{11}$, nitro, cyano, —OC$_{1-6}$ alkyl, —SC$_{1-6}$ alkyl, —C$_{1-6}$ alkyl, —C$_{2-6}$ alkenyl, —C$_{2-6}$ alkynyl, C(O)R$^{12}$, NR$^{13}$R$^{14}$, C$_{3-8}$ cycloalkyl or hydroxyl;

$R^8$ is H, halogen, —S(O)R$^{15}$, —S(O)$_2$R$^{11}$, nitro, cyano, —OC$_{1-6}$ alkyl, —SC$_{1-6}$ alkyl, —C$_{1-6}$ alkyl, —C$_{2-6}$ alkenyl, —C$_{2-6}$ alkynyl, C(O)R$^{12}$, NR$^{13}$R$^{14}$, C$_{3-8}$ cycloalkyl or hydroxyl;

$R^9$ is H, halogen, —S(O)R$^{15}$, —S(O)$_2$R$^{11}$, nitro, cyano, —OC$_{1-6}$ alkyl, —SC$_{1-6}$ alkyl, —C$_{1-6}$ alkyl, —C$_{2-6}$ alkenyl, —C$_{2-6}$ alkynyl, C(O)R$^{12}$, NR$^{13}$R$^{14}$, C$_{3-8}$ cycloalkyl or hydroxyl;

$R^{10}$ is H, halogen, —S(O)R$^{15}$, —S(O)$_2$R$^{11}$, nitro, cyano, —OC$_{1-6}$ alkyl, —SC$_{1-6}$ alkyl, —C$_{1-6}$ alkyl, —C$_{2-6}$ alkenyl, —C$_{2-6}$ alkynyl, C(O)R$^{12}$, NR$^{13}$R$^{14}$, C$_{3-8}$ cycloalkyl or hydroxyl;

X is O or S;
Y is O or S;
$R^{11}$ is H, hydroxyl, —C$_{1-6}$ alkyl, C$_{3-8}$ cycloalkyl or NR$^{13}$R$^{14}$;
$R^{12}$ is H, hydroxyl, —C$_{1-6}$ alkyl, hydroxyl, C$_{3-8}$ cycloalkyl, NR$^{13}$R$^{14}$ or —OC$_{1-6}$ alkyl;
$R^{13}$ is H, —C$_{1-6}$ alkyl, C$_{3-8}$ cycloalkyl, SO$_2$R$^{11}$ or C(O)R$^{16}$;
$R^{14}$ is H, —C$_{1-6}$ alkyl or C$_{3-8}$ cycloalkyl;
$R^{15}$ is —C$_{1-6}$ alkyl, or C$_{3-8}$ cycloalkyl;
$R^{16}$ is H, —C$_{1-6}$ alkyl or C$_{3-8}$ cycloalkyl;
n is 1-4; and
m is 1-4.

In another aspect, the invention provides a compound having Formula I wherein:
$R^{17}$ is

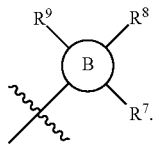

In another aspect, the invention provides a compound having Formula I wherein:

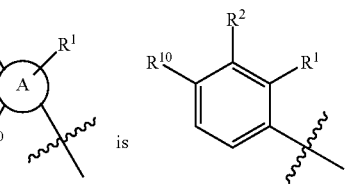

In another aspect, the invention provides a compound having Formula I wherein:
$R^{17}$ is

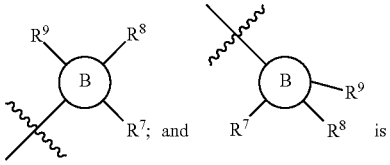

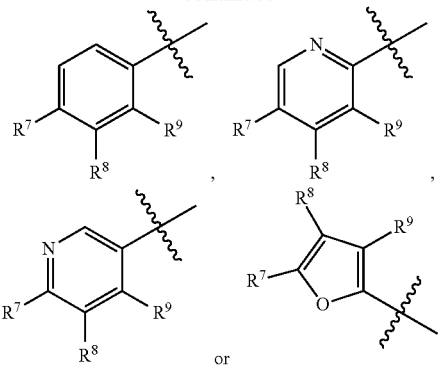

In another aspect, the invention provides a compound having Formula I wherein:

$R^{17}$ is

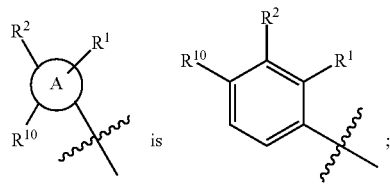

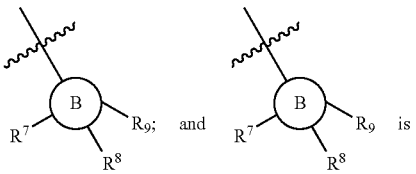

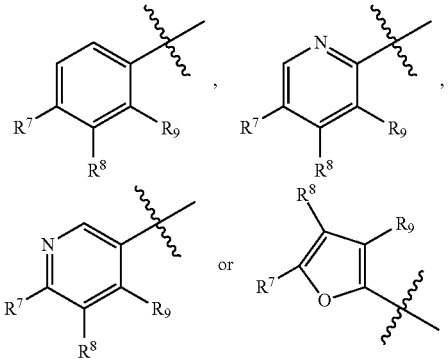

In another aspect, the invention provides a compound having Formula I wherein:
A is C$_{6-10}$ aryl;
$R^{17}$ is

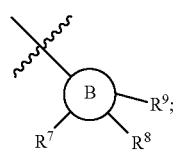

B is C$_{6-10}$ aryl, Heterocyle;
R$^1$ is H;
R$^2$ is H;
R$^3$ is H;
R$^4$ is H;
R$^{5a}$ is H;
R$^{5b}$ is H;
R$^{5c}$ is H;
R$^{5d}$ is H;
R$^6$ is H, —(CH$_2$)$_n$NR$^{13}$R$^{14}$, —(CH$_2$)$_m$ heterocycle or —C$_{1-6}$ alkyl;
R$^7$ is H, halogen or cyano;
R$^8$ is H or halogen;
R$^9$ is H;
R$^{19}$ is halogen, —S(O)R$^{15}$, —S(O)$_2$R$^{11}$, —SC$_{1-6}$ alkyl, —C$_{1-6}$ alkyl or C(O)R$^{12}$;
X is O;
Y is O;
R$^{11}$ is —C$_{1-6}$ alkyl;
R$^{12}$ is —C$_{1-6}$ alkyl;
R$^{13}$ is H or —C$_{1-6}$ alkyl;
R$^{14}$ is H or —C$_{1-6}$ alkyl;
R$^{15}$ is —C$_{1-6}$ alkyl;
n is 1-4; and
m is 1-4.

In another aspect, the invention provides a compound having Formula I wherein:

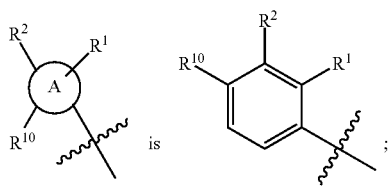

R$^{17}$ is C$_{1-6}$ alkyl;
R$^1$ is H;
R$^2$ is H;
R$^3$ is H;
R$^4$ is H;
R$^{5a}$ is H;
R$^{5b}$ is H;
R$^{5c}$ is H;
R$^{5d}$ is H;
R$^6$ is H, —(CH$_2$)$_n$NR$^{13}$R$^{14}$, —(CH$_2$)$_m$ heterocycle or —C$_{1-6}$ alkyl;
R$^{10}$ is halogen, —S(O)R$^{15}$, —S(O)$_2$R$^{11}$, —SC$_{1-6}$ alkyl, —C$_{1-6}$ alkyl or C(O)R$^{12}$;
X is O;
Y is O;
R$^{11}$ is —C$_{1-6}$ alkyl;
R$^{12}$ is —C$_{1-6}$ alkyl;
R$^{13}$ is H or —C$_{1-6}$ alkyl;
R$^{14}$ is H or —C$_{1-6}$ alkyl;
R$^{15}$ is —C$_{1-6}$ alkyl;
n is 1-4; and
m is 1-4.

In another aspect, the invention provides a compound having Formula I wherein:

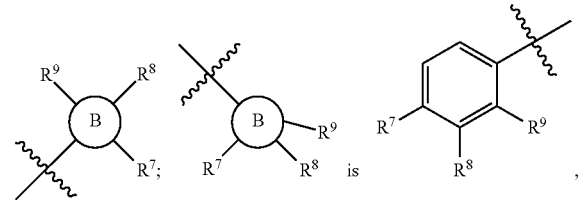

R$^{17}$ is

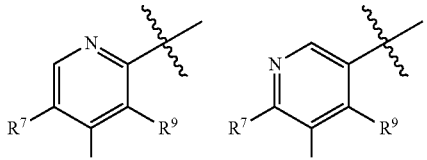

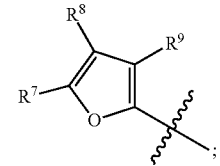

R$^1$ is H;
R$^2$ is H;
R$^3$ is H;
R$^4$ is H;
R$^{5a}$ is H;
R$^{5b}$ is H;
R$^{5c}$ is H;
R$^{5d}$ is H;
R$^6$ is H, —(CH$_2$)$_r$, NR$^{13}$R$^{14}$, —(CH$_2$)$_m$ heterocycle or —C$_{1-6}$ alkyl;
R$^7$ is H, halogen or cyano;
R$^8$ is H or halogen;
R$^9$ is H;
R$^{10}$ is halogen, —S(O)R$^{15}$, —S(O)$_2$R$^{11}$, —SC$_{1-6}$ alkyl, —C$_{1-6}$ alkyl or C(O)R$^{12}$;
X is O;
Y is O;
R$^{11}$ is —C$_{1-6}$ alkyl;
R$^{12}$ is —C$_{1-6}$ alkyl;
R$^{13}$ is H or —C$_{1-6}$ alkyl;
R$^{14}$ is H or —C$_{1-6}$ alkyl;
R$^{15}$ is —C$_{1-6}$ alkyl;
n is 1-4; and
m is 1-4.-

In another aspect, the invention provides a compound having Formula I wherein:

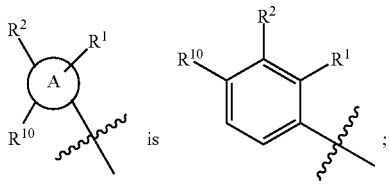

$R^{17}$ is

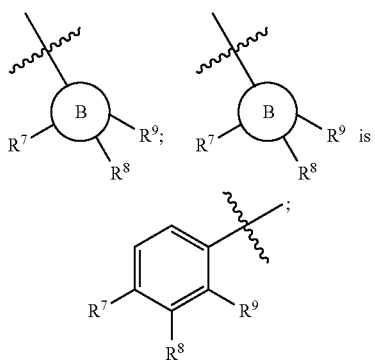

$R^1$ is H;
$R^2$ is H;
$R^3$ is H;
$R^4$ is H;
$R^{5a}$ is H;
$R^{5b}$ is H;
$R^{5c}$ is H;
$R^{5d}$ is H;
$R^6$ is H, —(CH$_2$)$_r$, NR$^{13}$R$^{14}$, —(CH$_2$)$_m$ heterocycle or —C$_{1-6}$ alkyl;
$R^7$ is halogen or cyano;
$R^8$ is H or halogen;
$R^9$ is H;
$R^{19}$ is halogen, —S(O)R$^{15}$, —S(O)$_2$R$^{11}$, —SC$_{1-6}$ alkyl, —C$_{1-6}$ alkyl or C(O)R$^{12}$;
X is O;
Y is O;
$R^{11}$ is —C$_{1-6}$ alkyl;
$R^{12}$ is —C$_{1-6}$ alkyl;
$R^{13}$ is H or —C$_{1-6}$ alkyl;
$R^{14}$ is H or —C$_{1-6}$ alkyl;
$R^{15}$ is —C$_{1-6}$ alkyl;
n is 1-4; and
m is 1-4.

In another aspect, the invention provides a compound having Formula I wherein:

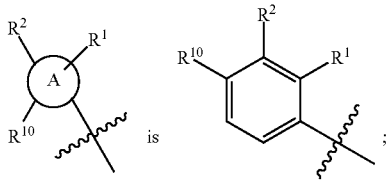

$R^{17}$ is

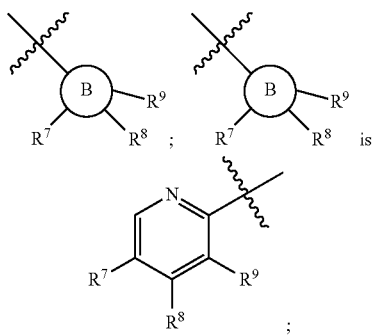

$R^1$ is H;
$R^2$ is H;
$R^3$ is H;
$R^4$ is H;
$R^{5a}$ is H;
$R^{5b}$ is H;
$R^{5c}$ is H;
$R^{5d}$ is H;
$R^6$ is H, —(CH$_2$)$_n$ NR$^{13}$R$^{14}$, —(CH$_2$)$_m$ heterocycle or —C$_{1-6}$ alkyl;
$R^7$ is halogen;
$R^8$ is H;
$R^9$ is H;
$R^{19}$ is —S(O)R$^{15}$, —S(O)$_2$R$^{11}$, —SC$_{1-6}$ alkyl, or C(O)R$^{12}$;
X is O;
Y is O;
$R^{11}$ is —C$_{1-6}$ alkyl;
$R^{12}$ is —C$_{1-6}$ alkyl;
$R^{13}$ is H or —C$_{1-6}$ alkyl;
$R^{14}$ is H or —C$_{1-6}$ alkyl;
$R^{15}$ is —C$_{1-6}$ alkyl;
n is 1-4; and
m is 1-4.

In another aspect, the invention provides a compound having Formula I wherein:

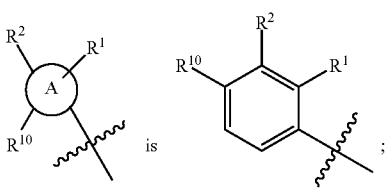

$R^{17}$ is

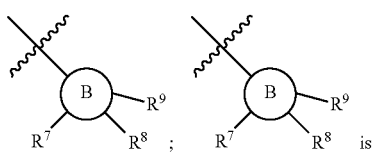

-continued

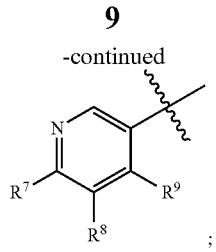

R¹ is H;
R² is H;
R³ is H;
R⁴ is H;
R⁵ᵃ is H;
R⁵ᵇ is H;
R⁵ᶜ is H;
R⁵ᵈ is H;
R⁶ is H, —(CH₂)ₙNR¹³R¹⁴, —(CH₂)ₘ heterocycle or —C₁₋₆ alkyl;
R⁷ is halogen;
R⁸ is H;
R⁹ is H;
R¹⁹ is —SC₁₋₆ alkyl or C(O)R¹²;
X is O;
Y is O;
R¹² is —C₁₋₆ alkyl;
R¹³ is H or —C₁₋₆ alkyl;
R¹⁴ is H or —C₁₋₆ alkyl;
n is 1-4; and
m is 1-4.

In another aspect, the invention provides a compound having Formula I wherein:

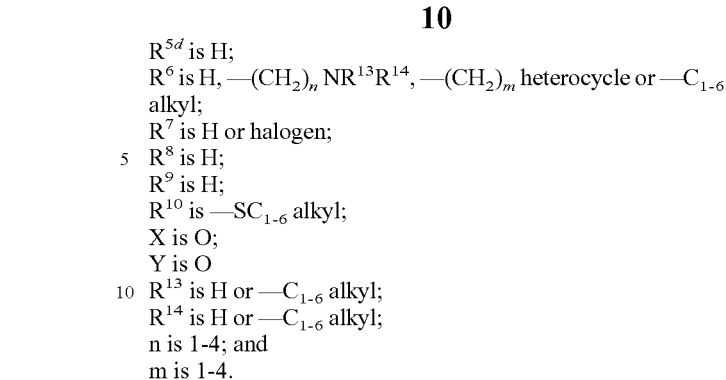

R¹⁷ is

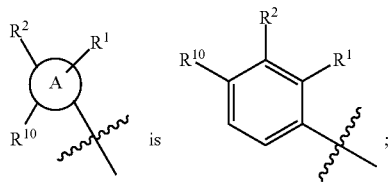

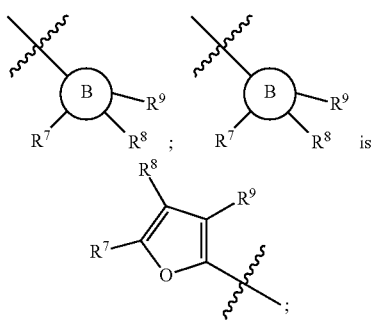

R¹ is H;
R² is H;
R³ is H;
R⁴ is H;
R⁵ᵃ is H;
R⁵ᵇ is H;
R⁵ᶜ is H;
R⁵ᵈ is H;
R⁶ is H, —(CH₂)ₙNR¹³R¹⁴, —(CH₂)ₘ heterocycle or —C₁₋₆ alkyl;
R⁷ is H or halogen;
R⁸ is H;
R⁹ is H;
R¹⁰ is —SC₁₋₆ alkyl;
X is O;
Y is O
R¹³ is H or —C₁₋₆ alkyl;
R¹⁴ is H or —C₁₋₆ alkyl;
n is 1-4; and
m is 1-4.

The term "alkyl", as used herein, refers to saturated, monovalent or divalent hydrocarbon moieties having linear or branched moieties or combinations thereof and containing 1 to 6 carbon atoms. One methylene (—CH₂—) group, of the alkyl can be replaced by oxygen, sulfur, sulfoxide, nitrogen, carbonyl, carboxyl, sulfonyl, —C(O)NH—, —S(O)₂NH—, by a divalent C₃₋₆ cycloalkyl, by a divalent heterocyle, or by a divalent aryl group. Alkyl groups can be independently substituted by halogen atoms, hydroxyl groups, cycloalkyl groups, amine groups, heterocyclic groups, carboxylic acid groups, phosphonic acid groups, sulphonic acid groups, phosphoric acid groups, nitro groups, amide groups, sulfonamides groups.

The term "cycloalkyl", as used herein, refers to a monovalent or divalent group of 3 to 8 carbon atoms derived from a saturated cyclic hydrocarbon. Cycloalkyl groups can be monocyclic or polycyclic. Cycloalkyl can be independently substituted by halogen, nitro groups, cyano groups, —OC₁₋₆ alkyl groups, —SC₁₋₆ alkyl groups, —C₁₋₆ alkyl groups, —C₂₋₆ alkenyl groups, —C₂₋₆ alkynyl groups, C₃₋₈ cycloalkyl groups, carboxylic acid groups, ester groups, ketone groups, aldehyde groups, amide groups, amine groups, sulfonamide groups or hydroxyl groups.

The term "cycloalkenyl", as used herein, refers to a monovalent or divalent group of 3 to 8 carbon atoms derived from a saturated cycloalkyl having at least one double bond. Cycloalkenyl groups can be monocyclic or polycyclic. Cycloalkenyl groups can be independently substituted by halogen atoms, nitro groups, cyano groups, —OC₁₋₆ alkyl groups, —SC₁₋₆ alkyl groups, —C₁₋₆ alkyl groups, —C₂₋₆ alkenyl groups, —C₂₋₆ alkynyl groups, carboxylic acid groups, ester groups, ketone groups, aldehyde groups, amide groups, amine groups, sulfonamide groups, C₃₋₈ cycloalkyl groups or hydroxyl groups.

The term "halogen", as used herein, refers to an atom of chlorine, bromine, fluorine, iodine.

The term "alkenyl", as used herein, refers to a monovalent or divalent hydrocarbon moiety having 2 to 6 carbon atoms, derived from a saturated alkyl, having at least one double bond. C₂₋₆ alkenyl can be in the E or Z configuration. Alkenyl groups can be substituted by C₁₋₃ alkyl, as defined above, or by halogen.

The term "alkynyl", as used herein, refers to a monovalent or divalent hydrocarbon radical having 2 to 6 carbon atoms, derived from a saturated alkyl, having at least one triple bond. Alkynyl groups can be substituted by C₁₋₃ alkyl, as defined above, or by halogen.

The term "heterocyle" as used herein, refers to a 3 to 10 membered ring, which can be aromatic or non-aromatic, saturated or unsaturated, containing at least one heteroatom selected from O or N or S or combinations of at least two thereof, interrupting the carbocyclic ring structure. The heterocyclic ring can be saturated or non-saturated. The heterocyclic ring can be interrupted by a C═O; the S and N heteroatoms can be oxidized. Heterocycles can be monocyclic or polycyclic. Heterocyclic ring moieties can be substituted by halogen, nitro groups, cyano groups, —$OC_{1-6}$ alkyl groups, —$SC_{1-6}$ alkyl groups, —$C_{1-6}$ alkyl groups, —$C_{2-6}$ alkenyl groups, —$C_{2-6}$ alkynyl groups, carboxylic acid groups, ester groups, ketone groups, aldehyde groups, amide groups, amine groups, sulfonamide groups, $C_{3-8}$ cycloalkyl groups or hydroxyl groups. Usually, in the present case, heterocyclic groups are 5 or 6 membered rings such as but not limited to: furan, 2-furyl and 3-furyl derivatives; thiophene, 2-thienyl and 3-thienyl derivatives; pyrrole, oxazole, thiazole, pyrrolidine, pyrroline, imidazole, pyrazole, pyrazoline, isoxazole, isothiazole, pyrazolidine, imidazoline, thiazoline, oxazoline, dihydrothiophene, 2-pyridyl, 3-pyridyl, 4-pyridyl, dihydrofuran, tetrazole, triazole, oxadiazole, 1,2,5-oxadiazole, thiadiazole, 1,2,3-triazole, 1,2,4-triazole, pyrrolidinone, pyrrol-2(3H)-one, imidazolidin-2-one, or 1,2,4-triazol-5(4H)-one and the like 5-membered heterocyclic rings.

The term "aryl" as used herein, refers to an organic moiety derived from an aromatic hydrocarbon consisting of a ring containing 6 to 10 carbon atoms by removal of one hydrogen, which can be substituted by halogen atoms, nitro groups, cyano groups, —$OC_{1-6}$ alkyl groups, —$SC_{1-6}$alkyl groups, —$C_{1-6}$ alkyl groups, —$C_{2-6}$ alkenyl groups, —$C_{2-6}$ alkynyl groups, carboxylic acid groups, ester groups, ketone groups, aldehyde groups, amide groups, amine groups, sulfonamide groups, $C_{3-8}$ cycloalkyl groups or hydroxyl groups. Usually aryl is phenyl. Preferred substitution site on aryl are the meta and the para positions. Most preferred substitution sites on aryl are the para positions.

The term "hydroxyl" as used herein, represents a group of formula "—OH".

The term "carbonyl" as used herein, represents a group of formula "—C(O)-".

The term "carboxyl" as used herein, represents a group of formula "—C(O)O—".

The term "sulfonyl" as used herein, represents a group of formula "—$SO_2^-$".

The term "sulfate" as used herein, represents a group of formula "—O—$S(O)_2$—O—".

The term "carboxylic acid" as used herein, represents a group of formula "—C(O)ON".

The term "nitro" as used herein, represents a group of formula "—$NO_2$".

The term "cyano" as used herein, represents a group of formula "—CN".

The term "amide" as used herein, represents a group of formula "—C(O)$NR^xR^y$," wherein $R^x$ and $R^y$ can be the same or independently H, alkyl, aryl, cycloalkyl, cycloalkenyl, heterocyle as defined above.

The term "amine" as used herein, represents a group of formula "—$NR^xR^y$", wherein $R^x$ and $R^y$ can be the same or independently H, alkyl, aryl, cycloalkyl, cycloalkenyl, heterocyle as defined above.

The term "ketone" as used herein, represents an organic compound having a carbonyl group linked to a carbon atom such as —(CO)$R^x$ wherein $R^x$ can be alkyl, aryl, cycloalkyl, cycloalkenyl, heterocyle as defined above.

The term "aldehyde" as used herein, represents a group of formula "—C(O)H".

The term "ester" as used herein, represents a group of formula "—C(O)$OR^x$",
wherein $R^x$ can be alkyl, aryl, cycloalkyl, cycloalkenyl, heterocyle as defined above.

The term "sulfonamide" as used herein, represents a group of formula "—$S(O)_2NR^xR^y$" wherein $R^x$ and $R^y$ can be the same or independently H, alkyl, aryl, cycloalkyl, cycloalkenyl, heterocyle as defined above.

The term "sulfoxide" as used herein, represents a group of formula "—S(O)—".

The term "phosphonic acid" as used herein, represents a group of formula "—P(O)(OH)$_2$".

The term "phosphoric acid" as used herein, represents a group of formula "—OP(O)(OH)$_2$".

The term "sulphonic acid" as used herein, represents a group of formula "—$S(O)_2OH$".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom.

Compounds of the invention are:

1-(4-acetylphenyl)-3-[2-(3-aminopropyl)-3-(4-cyanophenyl)-1-oxo-1,2,3,4-tetrahydroisoquinolin-7-yl]urea;

1-(4-acetylphenyl)-3-[2-(2-aminoethyl)-3-(4-cyanophenyl)-1-oxo-1,2,3,4-tetrahydroisoquinolin-7-yl]urea;

1-(4-acetylphenyl)-3-{3-(4-cyanophenyl)-2-[2-(1H-imidazol-4-yl)ethyl]-1-oxo-1,2,3,4-tetrahydroisoquinolin-7-yl}urea;

1-(4-acetylphenyl)-3-{3-(4-cyanophenyl)-2-[2-(methylamino)ethyl]-1-oxo-1,2,3,4-tetrahydroisoquinolin-7-yl}urea;

1-[2-(3-aminopropyl)-3-(4-cyanophenyl)-1-oxo-1,2,3,4-tetrahydroisoquinolin-7-yl]-3-[4-(trifluoromethyl)phenyl]urea;

1-{3-(4-cyanophenyl)-2-[2-(1H-imidazol-4-yl)ethyl]-1-oxo-1,2,3,4-tetrahydroisoquinolin-7-yl}-3-[4-(trifluoromethyl)phenyl]urea;

1-[2-(3-aminopropyl)-3-(4-cyanophenyl)-1-oxo-1,2,3,4-tetrahydroisoquinolin-7-yl]-3-[4-(methylthio)phenyl]urea;

1-(4-acetylphenyl)-3-{3-(3,4-dichlorophenyl)-2-[2-(1H-imidazol-4-yl)ethyl]-1-oxo-1,2,3,4-tetrahydroisoquinolin-7-yl}urea;

1-[2-(3-aminopropyl)-3-(4-cyanophenyl)-1-oxo-1,2,3,4-tetrahydroisoquinolin-7-yl]-3-(4-bromophenyl)urea;

1-[2-(3-aminopropyl)-3-(4-cyanophenyl)-1-oxo-1,2,3,4-tetrahydroisoquinolin-7-yl]-3-[4-(methylsulfinyl)phenyl]urea;

1-[2-(3-aminopropyl)-3-(4-cyanophenyl)-1-oxo-1,2,3,4-tetrahydroisoquinolin-7-yl]-3-[4-(methylsulfonyl)phenyl]urea;

1-{3-(4-cyanophenyl)-2-[2-(1H-imidazol-4-yl)ethyl]-1-oxo-1,2,3,4-tetrahydroisoquinolin-7-yl}-3-[4-(methylthio)phenyl]urea;

1-{3-(4-cyanophenyl)-2-[2-(1H-imidazol-4-yl)ethyl]-1-oxo-1,2,3,4-tetrahydroisoquinolin-7-yl}-3-[4-(methylsulfinyl)phenyl]urea;

1-{3-(4-cyanophenyl)-2-[2-(1H-imidazol-4-yl)ethyl]-1-oxo-1,2,3,4-tetrahydroisoquinolin-7-yl}-3-[4-(methylsulfonyl)phenyl]urea;

1-{3-(6-fluoropyridin-3-yl)-2-[2-(1H-imidazol-4-yl)ethyl]-1-oxo-1,2,3,4-tetrahydroisoquinolin-7-yl}-3-[4-(methylthio)phenyl]urea;

1-{3-(5-fluoropyridin-2-yl)-2-[2-(1H-imidazol-4-yl)ethyl]-1-oxo-1,2,3,4-tetrahydro isoquinolin-7-yl}-3-[4-(methylsulfinyl)phenyl]urea;

1-{3-(5-fluoropyridin-2-yl)-2-[2-(1H-imidazol-4-yl)ethyl]-1-oxo-1,2,3,4-tetrahydro isoquinolin-7-yl}-3-[4-(methylsulfonyl)phenyl]urea;

1-{3-(2-furyl)-2-[2-(1H-imidazol-4-yl)ethyl]-1-oxo-1,2,3,4-tetrahydroisoquinolin-7-yl}-3-[4-(methylthio)phenyl]urea;

1-{3-(5-chloro-2-furyl)-2-[2-(1H-imidazol-4-yl)ethyl]-1-oxo-1,2,3,4-tetrahydroisoquinolin-7-yl}-3-[4-(methylthio)phenyl]urea;

1-(4-acetylphenyl)-3-{3-(6-chloropyridin-3-yl)-2-[2-(1H-imidazol-4-yl)ethyl]-1-oxo-1,2,3,4-tetrahydroisoquinolin-7-yl}urea;

1-{3-(6-chloropyridin-3-yl)-2-[2-(1H-imidazol-4-yl)ethyl]-1-oxo-1,2,3,4-tetrahydroisoquinolin-7-yl}-3-[4-(methylthio)phenyl]urea;

1-(4-acetylphenyl)-3-{3-(5-chloropyridin-2-yl)-2-[2-(1H-imidazol-4-yl)ethyl]-1-oxo-1,2,3,4-tetrahydroisoquinolin-7-yl}urea;

1-{3-(5-chloropyridin-2-yl)-2-[2-(1H-imidazol-4-yl)ethyl]-1-oxo-1,2,3,4-tetrahydro isoquinolin-7-yl}-3-[4-(methylthio)phenyl]urea;

1-{3-(5-chloropyridin-2-yl)-2-[2-(1H-imidazol-4-yl)ethyl]-1-oxo-1,2,3,4-tetrahydro isoquinolin-7-yl}-3-[4-(methylsulfonyl)phenyl]urea;

1-[2-(3-aminopropyl)-3-(4-cyanophenyl)-1-oxo-1,2,3,4-tetrahydroisoquinolin-7-yl]-3-[4-(ethylthio)phenyl]urea;

(S)-1-[2-(3-aminopropyl)-3-(4-cyanophenyl)-1-oxo-1,2,3,4-tetrahydroisoquinolin-7-yl]-3-[4-(methylthio)phenyl]urea;

(R)-1-[2-(3-aminopropyl)-3-(4-cyanophenyl)-1-oxo-1,2,3,4-tetrahydroisoquinolin-7-yl]-3-[4-(methylthio)phenyl]urea;

(S)-1-[2-(3-aminopropyl)-3-(4-cyanophenyl)-1-oxo-1,2,3,4-tetrahydroisoquinolin-7-yl]-3-[4-(methylsulfinyl)phenyl]urea;

(S)-1-[2-(3-aminopropyl)-3-(4-cyanophenyl)-1-oxo-1,2,3,4-tetrahydroisoquinolin-7-yl]-3-[4-(methylsulfinyl)phenyl]urea;

(S)-1-[2-(3-aminopropyl)-3-(4-cyanophenyl)-1-oxo-1,2,3,4-tetrahydroisoquinolin-7-yl]-3-[4-(methylsulfonyl)phenyl]urea;

(R)-1-[2-(3-aminopropyl)-3-(4-cyanophenyl)-1-oxo-1,2,3,4-tetrahydroisoquinolin-7-yl]-3-[4-(methylsulfonyl)phenyl]urea;

1-[2-(3-aminopropyl)-3-methyl-1-oxo-1,2,3,4-tetrahydroisoquinolin-7-yl]-3-[4-(methylthio)phenyl]urea;

1-[2-(3-aminopropyl)-3-methyl-1-oxo-1,2,3,4-tetrahydroisoquinolin-7-yl]-3-[4-(methylsulfonyl)phenyl]urea.

Preferred compounds of the invention are:

1-(4-acetylphenyl)-3-{3-(4-cyanophenyl)-2-[2-(1H-imidazol-4-yl)ethyl]-1-oxo-1,2,3,4-tetrahydroisoquinolin-7-yl}urea;

1-[2-(3-aminopropyl)-3-(4-cyanophenyl)-1-oxo-1,2,3,4-tetrahydroisoquinolin-7-yl]-3-[4-(trifluoromethyl)phenyl]urea;

1-[2-(3-aminopropyl)-3-(4-cyanophenyl)-1-oxo-1,2,3,4-tetrahydroisoquinolin-7-yl]-3-[4-(methylthio)phenyl]urea;

1-(4-acetylphenyl)-3-{3-(3,4-dichlorophenyl)-2-[2-(1H-imidazol-4-yl)ethyl]-1-oxo-1,2,3,4-tetrahydroisoquinolin-7-yl}urea;

1-[2-(3-aminopropyl)-3-(4-cyanophenyl)-1-oxo-1,2,3,4-tetrahydroisoquinolin-7-yl]-3-(4-bromophenyl)urea;

1-[2-(3-aminopropyl)-3-(4-cyanophenyl)-1-oxo-1,2,3,4-tetrahydroisoquinolin-7-yl]-3-[4-(methylsulfinyl)phenyl]urea;

1-[2-(3-aminopropyl)-3-(4-cyanophenyl)-1-oxo-1,2,3,4-tetrahydroisoquinolin-7-yl]-3-[4-(methylsulfonyl)phenyl]urea;

1-{3-(4-cyanophenyl)-2-[2-(1H-imidazol-4-yl)ethyl]-1-oxo-1,2,3,4-tetrahydroisoquinolin-7-yl}-3-[4-(methylsulfinyl)phenyl]urea;

1-{3-(4-cyanophenyl)-2-[2-(1H-imidazol-4-yl)ethyl]-1-oxo-1,2,3,4-tetrahydroisoquinolin-7-yl}-3-[4-(methylsulfonyl)phenyl]urea;

1-{3-(6-fluoropyridin-3-yl)-2-[2-(1H-imidazol-4-yl)ethyl]-1-oxo-1,2,3,4-tetrahydroisoquinolin-7-yl}-3-[4-(methylthio)phenyl]urea;

1-{3-(5-fluoropyridin-2-yl)-2-[2-(1H-imidazol-4-yl)ethyl]-1-oxo-1,2,3,4-tetrahydro isoquinolin-7-yl}-3-[4-(methylsulfinyl)phenyl]urea;

1-{3-(5-fluoropyridin-2-yl)-2-[2-(1H-imidazol-4-yl)ethyl]-1-oxo-1,2,3,4-tetrahydro isoquinolin-7-yl}-3-[4-(methylsulfonyl)phenyl]urea;

(S)-1-[2-(3-aminopropyl)-3-(4-cyanophenyl)-1-oxo-1,2,3,4-tetrahydroisoquinolin-7-yl]-3-[4-(methylthio)phenyl]urea;

1-{3-(2-furyl)-2-[2-(1H-imidazol-4-yl)ethyl]-1-oxo-1,2,3,4-tetrahydroisoquinolin-7-yl}-3-[4-(methylthio)phenyl]urea;

1-{3-(5-chloro-2-furyl)-2-[2-(1H-imidazol-4-yl)ethyl]-1-oxo-1,2,3,4-tetrahydroisoquinolin-7-yl}-3-[4-(methylthio)phenyl]urea;

1-{3-(5-chloropyridin-2-yl)-2-[2-(1H-imidazol-4-yl)ethyl]-1-oxo-1,2,3,4-tetrahydro isoquinolin-7-yl}-3-[4-(methylsulfonyl)phenyl]urea;

1-{3-(5-chloropyridin-2-yl)-2-[2-(1H-imidazol-4-yl)ethyl]-1-oxo-1,2,3,4-tetrahydro isoquinolin-7-yl}-3-[4-(methylthio)phenyl]urea;

1-[2-(3-aminopropyl)-3-(4-cyanophenyl)-1-oxo-1,2,3,4-tetrahydroisoquinolin-7-yl]-3-[4-(ethylthio)phenyl]urea;

1-{3-(6-chloropyridin-3-yl)-2-[2-(1H-imidazol-4-yl)ethyl]-1-oxo-1,2,3,4-tetrahydroisoquinolin-7-yl}-3-[4-(methylthio)phenyl]urea;

(R)-1-[2-(3-aminopropyl)-3-(4-cyanophenyl)-1-oxo-1,2,3,4-tetrahydroisoquinolin-7-yl]-3-[4-(methylthio)phenyl]urea;

1-[2-(3-aminopropyl)-3-methyl-1-oxo-1,2,3,4-tetrahydroisoquinolin-7-yl]-3-[4-(methylthio)phenyl]urea.

Most Preferred compounds of the invention are:

1-(4-acetylphenyl)-3-{3-(4-cyanophenyl)-2-[2-(1H-imidazol-4-yl)ethyl]-1-oxo-1,2,3,4-tetrahydroisoquinolin-7-yl}urea;

1-[2-(3-aminopropyl)-3-(4-cyanophenyl)-1-oxo-1,2,3,4-tetrahydroisoquinolin-7-yl]-3-[4-(methylthio)phenyl]urea;

1-[2-(3-aminopropyl)-3-(4-cyanophenyl)-1-oxo-1,2,3,4-tetrahydroisoquinolin-7-yl]-3-[4-(methylsulfonyl)phenyl]urea;

1-{3-(6-fluoropyridin-3-yl)-2-[2-(1H-imidazol-4-yl)ethyl]-1-oxo-1,2,3,4-tetrahydroisoquinolin-7-yl}-3-[4-(methylthio)phenyl]urea;

1-{3-(5-fluoropyridin-2-yl)-2-[2-(1H-imidazol-4-yl)ethyl]-1-oxo-1,2,3,4-tetrahydro isoquinolin-7-yl}-3-[4-(methylsulfinyl)phenyl]urea;

1-{3-(5-fluoropyridin-2-yl)-2-[2-(1H-imidazol-4-yl)ethyl]-1-oxo-1,2,3,4-tetrahydro isoquinolin-7-yl}-3-[4-(methylsulfonyl)phenyl]urea;

1-{3-(6-chloropyridin-3-yl)-2-[2-(1H-imidazol-4-yl)ethyl]-1-oxo-1,2,3,4-tetrahydroisoquinolin-7-yl}-3-[4-(methylthio)phenyl]urea;

1-{3-(5-chloropyridin-2-yl)-2-[2-(1H-imidazol-4-yl)ethyl]-1-oxo-1,2,3,4-tetrahydro isoquinolin-7-yl}-3-[4-(methylsulfonyl)phenyl]urea;

1-[2-(3-aminopropyl)-3-(4-cyanophenyl)-1-oxo-1,2,3,4-tetrahydroisoquinolin-7-yl]-3-[4-(ethylthio)phenyl]urea;

(S)-1-[2-(3-aminopropyl)-3-(4-cyanophenyl)-1-oxo-1,2,3,4-tetrahydroisoquinolin-7-yl]-3-[4-(methylthio)phenyl]urea;

1-[2-(3-aminopropyl)-3-methyl-1-oxo-1,2,3,4-tetrahydroisoquinolin-7-yl]-3-[4-(methylthio)phenyl]urea.

Some compounds of Formula I and some of their intermediates have at least one asymmetric center in their structure. This asymmetric center may be present in an R or S configuration, said R and S notation is used in correspondence with the rules described in Pure Appli. Chem. (1976), 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I are able to form.

The acid addition salt form of a compound of Formula I that occurs in its free form as a base can be obtained by treating the free base with an appropriate acid such as an inorganic acid, for example, hydrochloric acid, hydrobromic acid, sulfuric acid, phosphoric acid, nitric acid and the like; or an organic acid such as for example, acetic acid, hydroxyacetic acid, propanoic acid, lactic acid, pyruvic acid, malonic acid, fumaric acid, maleic acid, oxalic acid, tartaric acid, succinic acid, malic acid, ascorbic acid, benzoic acid, tannic acid, pamoic acid, citric acid, methylsulfonic acid, ethanesulfonic acid, benzenesulfonic acid, formic and the like (Handbook of Pharmaceutical Salts, P. Heinrich Stahal & Camille G. Wermuth (Eds), Verlag Helvetica Chemica Acta-Zürich, 2002, 329-345).

The base addition salt form of a compound of Formula I that occurs in its acid form can be obtained by treating the acid with an appropriate base such as an inorganic base, for example, sodium hydroxide, magnesium hydroxide, potassium hydroxide, Calcium hydroxide, ammonia and the like; or an organic base such as for example, L-Arginine, ethanolamine, betaine, benzathine, morpholine and the like. (Handbook of Pharmaceutical Salts, P. Heinrich Stahal & Camille G. Wermuth (Eds), Verlag Helvetica Chemica Acta-Zürich, 2002, 329-345).

Compounds of Formula I and their salts can be in the form of a solvate, which is included within the scope of the present invention. Such solvates include for example hydrates, alcoholates and the like.

With respect to the present invention reference to a compound or compounds, is intended to encompass that compound in each of its possible isomeric forms and mixtures thereof unless the particular isomeric form is referred to specifically.

Compounds according to the present invention may exist in different polymorphic forms. Although not explicitly indicated in the above formula, such forms are intended to be included within the scope of the present invention.

The compounds of the invention are indicated for use in treating or preventing conditions in which there is likely to be a component involving the N-formyl peptide receptor like-1 receptor.

In another embodiment, there are provided pharmaceutical compositions including at least one compound of the invention in a pharmaceutically acceptable carrier.

In a further embodiment of the invention, there are provided methods for treating disorders associated with modulation of the N-formyl peptide receptor like-1 receptor.

Such methods can be performed, for example, by administering to a subject in need thereof a pharmaceutical composition containing a therapeutically effective amount of at least one compound of the invention.

Therapeutic utilities of the N-formyl peptide receptor like-1 receptor modulators are ocular inflammatory diseases including, but not limited to, wet and dry age-related macular degeneration (ARMD), uveitis, dry eye, Keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy (proliferative), retinopathy of prematurity (ROP), acute macular neuroretinopathy, central serous chorioretinopathy, cystoid macular edema, and diabetic macular edema; infectious keratitis, uveitis, herpetic keratitis, corneal angiogenesis, lymphangiogenesis, uveitis, retinitis, and choroiditis such as acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi- and Harada syndrome; vasuclar diseases/exudative diseases such as retinal arterial occlusive disease, central retinal vein occlusion, cystoids macular edema, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, post surgical corneal wound healing, conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (PONS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with accosiated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigement epitheliitis, systemic inflammatory diseases such as stroke, coronary artery disease, obstructive airway diseases, HIV-mediated retroviral infections, cardiovascular disorders including coronary artery disease, neuroinflammation, neurological disorders, pain and immunological disorders, asthma, allergic disorders, inflammation, systemic lupus erythematosus, eczema, psoriasis, CNS disorders such as Alzheimer's disease, arthritis, sepsis, inflammatory bowel disease, cachexia, angina pectoris, post-surgical corneal inflammation, blepharitis, MGD, dermal wound healing, burns, rosacea, atopic dermatitis, acne, psoriasis, seborrheic dermatitis, actinic keratoses, viral warts, photoaging rheumatoid arthritis and related inflammatory disorders, alopecia, glaucoma, branch vein occlusion, Best's vitelliform macular degenartion, retinitis pigmentosa, proliferative vitreoretinopathy (PVR), and any other degenerative disease of either the photoreceptors or the RPE (Perretti, Mauro et al. Pharmacology & Therapeutics 127 (2010) 175-188.)

These compounds are useful for the treatment of mammals, including humans, with a range of conditions and diseases that are alleviated by the N-formyl peptide receptor like-1 receptor modulation: including, but not limited to the treatment of wet and dry age-related macular degeneration (ARMD), diabetic retinopathy (proliferative), retinopathy of prematurity (ROP), diabetic macular edema, uveitis, retinal vein occlusion, cystoids macular edema, glaucoma, branch vein occlusion, Best's vitelliform macular degenartion, retinitis pigmentosa, proliferative vitreoretinopathy (PVR), and any other degenerative disease of either the photoreceptors or the RPE.

In still another embodiment of the invention, there are provided methods for treating disorders associated with modulation of the FPRL-1 receptor. Such methods can be performed, for example, by administering to a subject in need thereof a therapeutically effective amount of at least one compound of the invention, or any combination thereof, or pharmaceutically acceptable salts, hydrates, solvates, crystal forms and individual isomers, enantiomers, and diastereomers thereof.

The present invention concerns the use of a compound of Formula I or a pharmaceutically acceptable salt thereof, for the manufacture of a medicament for the treatment of ocular inflammatory diseases including, but not limited to, wet and dry age-related macular degeneration (ARMD), uveitis, dry eye, Keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy (proliferative), retinopathy of prematurity (ROP), acute macular neuroretinopathy, central serous chorioretinopathy, cystoid macular edema, and diabetic macular edema; infectious keratitis, uveitis, herpetic keratitis, corneal angiogenesis, lymphangiogenesis, uveitis, retinitis, and choroiditis such as acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi- and Harada syndrome; vasuclar diseases/exudative diseases such as retinal arterial occlusive disease, central retinal vein occlusion, cystoids macular edema, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, post-sugical corneal wound healing, conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (PONS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with accosiated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigment epitheliitis, systemic inflammatory diseases such as stroke, coronary artery disease, obstructive airway diseases, HIV-mediated retroviral infections, cardiovascular disorders including coronary artery disease, neuroinflammation, neurological disorders, pain and immunological disorders, asthma, allergic disorders, inflammation, systemic lupus erythematosus, eczema, psoriasis, CNS disorders such as Alzheimer's disease, arthritis, sepsis, inflammatory bowel disease, cachexia, angina pectoris, post-surgical corneal inflammation, blepharitis, MGD, dermal wound healing, burns, rosacea, atopic dermatitis, acne, psoriasis, seborrheic dermatitis, actinic keratoses, viral warts, photoaging rheumatoid arthritis and related inflammatory disorders, alopecia, glaucoma, branch vein occlusion, Best's vitelliform macular degenartion, retinitis pigmentosa, proliferative vitreoretinopathy (PVR), and any other degenerative disease of either the photoreceptors or the RPE.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, direct injection, application at the back of the eye or formulations that may further enhance the long duration of actions such as a slow releasing pellet, suspension, gel, or sustained delivery devices such as any suitable drug delivery system (DDS) known in the art. While topical administration is preferred, this compound may also be used in an intraocular implant as described in U.S. U.S. Pat. No. 7,931,909, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

The compounds of the invention may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The compounds and pharmaceutical compositions described herein are useful as medicaments in mammals, including humans, for treatment of diseases and/or alleviations of conditions which are responsive to treatment by agonists or functional antagonists of the N-formyl peptide receptor like-1 (FPRL-1) receptor. Thus, in further embodiments of the invention, there are provided methods for treating a disorder associated with modulation of the N-formyl peptide receptor like-1 (FPRL-1) receptor. Such methods can be performed, for example, by administering to a subject in need thereof a pharmaceutical composition containing a therapeutically effective amount of at least one invention compound. As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

The present invention concerns also processes for preparing the compounds of Formula I. The compounds of formula I according to the invention can be prepared analogously to conventional methods as understood by the person skilled in the art of synthetic organic chemistry. Synthetic Scheme 1 set forth below, illustrates how the compounds according to the invention can be made.

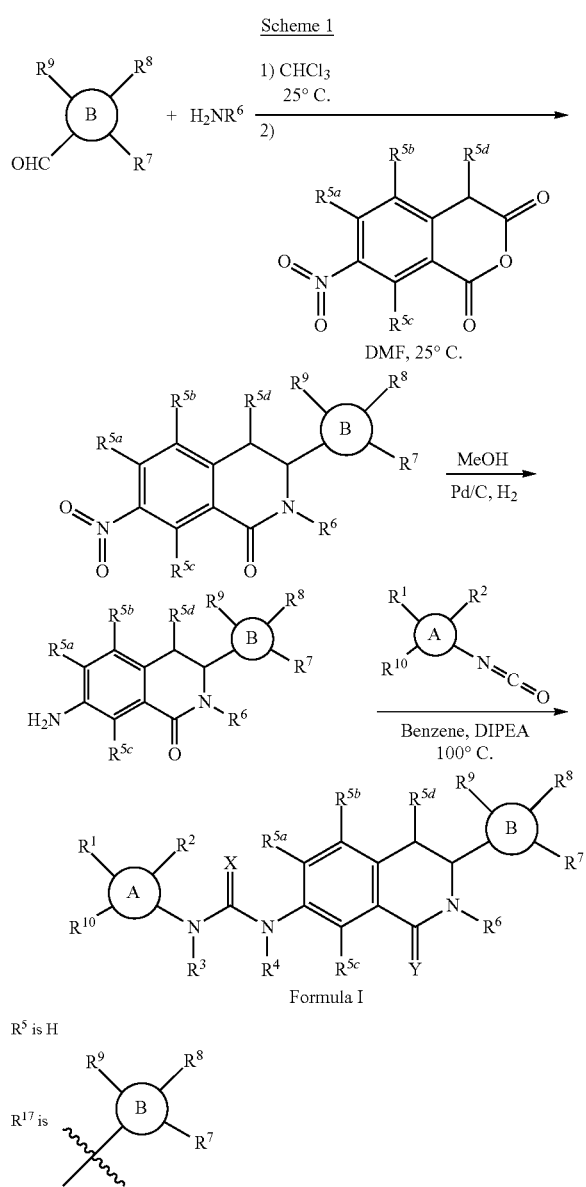

Scheme 1

Compounds within the scope of the invention may be prepared as depicted in Scheme 1. In general, an aldehyde, such as 4-cyanobenzaldehyde, and an amine, such as $N^1$-boc-1,3-diamino-n-propane can be reacted in a suitable solvent (eg., THF or chloroform) to form an imine intermediate. The solvent may then be evaporated under reduced pressure, and the residue redissolved in DMF. The imine is then reacted with 7-nitro-homopthallic anhydride, (i.e., 7-Nitro-1H-2-benzopyran-1,3(4H)-dione) to produce a 7-nitro-3,4-dihydroisoquinolin-1(2H)-one, such as tert-butyl (3-(3-(4-cyanophenyl)-7-nitro-1-oxo-3,4-dihydroisoquinolin-2(1H)-yl)propyl) carbamate (Intermediate 1). The nitro group of the 7-nitro-3,4-dihydroisoquinolin-1(2H)-one can then be treated with a reducing agent, such as hydrogen in the presence of 10% palladium on carbon, in a suitable solvent (MeOH) to give a 7-amino-3,4-dihydroisoquinolin-1(2H)-one, such as tert-butyl (3-(7-amino-3-(4-cyanophenyl)-1-oxo-3,4-dihydroisoquinolin-2(1H)-yl)propyl)carbamate (Intermediate 13). The 7-amino-3,4-dihydroisoquinolin-1(2H)-one may be dissolved in a suitable solvent (eg., benzene) and then be treated with an organic isocyanates, such as 4-acetylphenyl isocyanates, in the presence of a strong base (eg, DIPEA) to produce a urea, such as tert-butyl {3-[7-({[(4-acetylphenyl)amino]carbonyl}amino)-3-(4-cyanophenyl)-1-oxo-3,4-dihydroisoquinolin-2(1H)-yl]propyl}carbamate (Intermediate 23), a compound which falls under the scope of the invention. At this stage, those skilled in the art will appreciate that many additional compounds that fall under the scope of the invention may be prepared by performing various common chemical reactions. For instance, a sulfide group may be oxidized to sulfoxide or sulfone groups by treatment with a suitable oxidizing agent (eg., m-chloroperbenzoic acid). Or, for example, the t-butylcarbamate group may be removed by treatment with a strong acid, such as trifluoroacetic acid, to give an amine product, such as 1-(4-acetyl phenyl)-3-[2-(2-aminoethyl)-3-(4-cyanophenyl)-1-oxo-1,2,3,4-tetrahydroisoquinolin-7-yl]urea (Compound 2). Details of certain specific chemical transformations are provided in the examples.

Those skilled in the art will be able to routinely modify and/or adapt the following scheme to synthesize any compounds of the invention covered by Formula I.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2$H (or D) in place of protium $^1$H (or H) or use of $^{13}$C enriched material in place of $^{12}$C and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following examples are for illustrative purposes only and are not intended, nor should they be construed as limiting the invention in any manner. Those skilled in the art will appreciate that variations and modifications of the following examples can be made without exceeding the spirit or scope of the invention.

As will be evident to those skilled in the art, individual isomeric forms can be obtained by separation of mixtures thereof in conventional manner. For example, in the case of diasteroisomeric isomers, chromatographic separation may be employed.

Compound names were generated with ACD version 11.0; and Intermediates and reagent names used in the examples were generated with softwares such as Chem Bio Draw Ultra version 12.0, ACD version 11.0 or Auto Nom 2000 from MDL ISIS Draw 2.5 SP1.

In general, characterization of the compounds is performed using NMR spectra, recorded on 300 and/or 600 MHz Varian and acquired at room temperature.

Chemical shifts are given in ppm referenced either to internal TMS or to the solvent signal. The optical rotation was recorded on Perkin Elmer Polarimeter 341, 589 nm at 20° C., Na/Hal lamp.

All the reagents, solvents, catalysts for which the synthesis is not described are purchased from chemical vendors such as Sigma Aldrich, Fluka, Bio-Blocks, Combi-blocks, TCI, VWR, Lancaster, Oakwood, Trans World Chemical, Alfa, Fisher, Maybridge, Frontier, Matrix, Ukrorgsynth, Toronto, Ryan Scientific, SiliCycle, Anaspec, Syn Chem, Chem-Impex, MIC-scientific, Ltd; however some known intermediates, were prepared according to published procedures.

Usually the compounds of the invention were purified by column chromatography (Auto-column) on an Teledyne-ISCO CombiFlash with a silica column, unless noted otherwise.

The chiral resolution was performed using chiral HPLC:
Preparative methods: Chiralpak AD-H (2×15 cm)
  30% ethanol/CO2, 100 Bar
  65 ml/min, 220 nm.
Analytical method: Chiralpak AD-H (25×0.46 cm)
  40% ethanol (DEA)/$CO_2$, 100 Bar
  3 ml/min, 220 nm.

The following abbreviations are used in the examples:
$NH_3$ ammonia
$CH_3CN$ acetonitrile
DMF N,N-dimethylformamide
MeOH methanol
$CD_3OD$ deuterated methanol
$Na_2SO_4$ sodium sulfate
EtOAc ethyl acetate
mW microwave Biotage Initiator Eight
Auto-column automated flash liquid chromatography
TFA trifluoroacetic acid
THF tetrahydrofuran
$Na_2CO_3$ sodium carbonate
N normality
Pd/C palladium(0) on carbon
EtOH ethanol
$SnCl_2$ stannous chloride
$Pd_2(dba)_3$ Tris(dibenzylideneacetone)dipalladium(0)
Xantphos 4,5-Bis(diphenylphosphino)-9,9-dimethylxanthene
boc tert-Butyloxycarbonyl The following synthetic schemes illustrate how compounds according to the invention can be made. Those skilled in the art will be routinely able to modify and/or adapt the following schemes to synthesize any compound of the invention covered by Formula I.

Example 1

Intermediate 1 tert-butyl (3-(3-(4-cyanophenyl)-7-nitro-1-oxo-3,4-dihydroisoquinolin-2(1H)-yl)propyl)carbamate To a solution of 4-cyanobenzaldehyde (150 mg, 1.15 mmol) in 6 mL of anhydrous THF was added $N^1$-boc-1,3-diamino-n-propane (219 mg, 1.27 mmol) and the mixture was stirred at 25° C. for 30 minutes. The solvent was evaporated and then 2 mL of DMF and 7-nitro-1H-2-benzopyran-1,3(4H)-dione (CAS 36795-25-2) (288 mg, 1.15 mmol) were added. Mixture was stirred at 25° C. for 12 hours. The solvent was evaporated and the residue was purified by medium pressure liquid chromatography on silica gel using ethyl acetate: hexane (8:2) to yield Intermediate 1 as a yellow solid.

$^1$H NMR (300 MHz, $CD_3OD$) δ: 8.80 (d, J=2.3 Hz, 1H), 8.24 (dd, J=8.2, 2.3 Hz, 1H), 7.63 (d, J=8.2 Hz, 2H), 7.36 (d, J=8.2 Hz, 1H), 7.30 (d, J=8.2 Hz, 2H), 5.24 (d, J=6.7 Hz, 1H), 4.07-4.22 (m, 1H), 3.79-3.91 (m, 1H), 3.31-3.37 (m, 1H), 3.15-3.23 (m, 1H), 3.03-3.13 (m, 1H), 2.89-2.98 (m, 1H), 1.78-1.90 (m, 2H), 1.41 (s, 9H).

Intermediates 2, 3, 4, 5, 6, 7, 8, 9, 10, 11 and 12 were prepared from the corresponding starting materials and 7-nitro-1H-2-benzopyran-1,3(4H)-dione in a similar manner to the procedure described in Example 1 for Intermediate 1. The reagents, reactants used and the results are described below in Table 1.

TABLE 1

| Interm. No. | IUPAC name | Reagent(s) Reactant(s) | $^1$H NMR δ (ppm) for Intermediate | Features |
|---|---|---|---|---|
| 2 | tert-butyl (2-(3-(4-cyanophenyl)-7-nitro-1-oxo-3,4-dihydroisoquinolin-2(1H)-yl)ethyl)carbamate | 4-cyanobenzaldehyde 1-boc-ethylenediamine anhydrous THF | $^1$H NMR (300 MHz, $CD_3OD$) δ: 8.73-8.87 (m, 1H), 8.16-8.34 (m, 2H), 7.92-8.04 (m, 1H), 7.63 (d, J = 8.2 Hz, 2H), 7.32 (s, 1H), 5.19-5.30 (m, 1H), 4.18-4.42 (m, 1H), 3.81-4.02 (m, 1H), 3.38-3.60 (m, 2H), 2.90-3.05 (m, 2H), 1.37 (s, 9H) | yellow solid |
| 3 | 4-(2-(2-(1H-imidazol-4-yl)ethyl)-7-nitro-1-oxo-1,2,3,4-tetrahydroisoquinolin-3-yl)benzonitrile | 4-cyanobenzaldehyde histamine anhydrous THF | $^1$H NMR (300 MHz, $CD_3OD$) δ: 2.87-2.98 (m, 1 H), 2.99-3.11 (m, 1 H), 3.15-3.28 (m, 2 H), 3.61 (dd, J = 16.7, 6.74 Hz, 1 H), 4.28-4.44 (m, 1 H), 4.98 (d, J = 5.3 Hz, 1 H), 6.91 (s, 1 H), 7.26 (d, J = 8.2 Hz, 2 H), 7.33 (d, J = 8.5 Hz, 1 H), 7.59 (s, 1 | pink solid |

TABLE 1-continued

| Interm. No. | IUPAC name | Reagent(s) Reactant(s) | $^1$H NMR δ (ppm) for Intermediate | Features |
|---|---|---|---|---|
| | | | H), 7.61-7.66 (m, 2 H), 8.23 (dd, J = 8.4, 2.5 Hz, 1 H), 8.79 (d, J = 2.3 Hz, 1 H) | |
| 4 | tert-butyl (2-(3-(4-cyanophenyl)-7-nitro-1-oxo-3,4-dihydroisoquinolin-2(1H)-yl)ethyl)(methyl)carbamate | 4-cyanobenzaldehyde N-boc-N-methylethylene diamine anhydrous THF | $^1$H NMR (300 MHz, CD$_3$OD) δ: 2.65-2.88 (m, 1 H), 2.95 (s, 3 H), 3.11-3.25 (m, 1 H), 3.36-3.47 (m, 1 H), 3.68-3.86 (m, 1 H), 3.87-4.06 (m, 1 H), 4.51-4.72 (m, 1 H), 5.27 (dd, J = 5.0, 4.4 Hz, 1 H), 7.32 (d, J = 8.2 Hz, 2 H), 7.36-7.40 (m, 1 H), 7.64 (d, J = 8.2 Hz, 2 H), 8.20-8.30 (m, 1 H), 8.79 (d, J = 3.5 Hz, 1 H) | yellow solid |
| 5 | 2-(2-(1H-imidazol-4-yl)ethyl)-3-(3,4-dichlorophenyl)-7-nitro-3,4-dihydroisoquinolin-1(2H)-one | 3,4-dichlorobenzaldehyde histamine anhydrous THF | $^1$H NMR (300 MHz, CD$_3$OD) δ: 2.85-3.11 (m, 2 H), 3.16-3.27 (m, 2 H), 3.50-3.62 (m, 1 H), 4.35 (dd, J = 18.8, 7.9 Hz, 1 H), 4.89 (d, J = 4.7 Hz, 1 H), 6.90 (s, 1 H), 6.95 (dd, J = 8.5, 2.1 Hz, 1 H), 7.26 (d, J = 2.1 Hz, 1 H), 7.36 (d, J = 8.8 Hz, 1 H), 7.37 (d, J = 8.2 Hz, 1 H), 7.61 (d, J = 1.2 Hz, 1 H), 8.25 (dd, J = 8.2, 2.3 Hz, 1 H), 8.79 (d, J = 2.6 Hz, 1 H) | orange solid |
| 6 | 2-(2-(1H-imidazol-4-yl)ethyl)-3-(5-fluoropyridin-2-yl)-7-nitro-3,4-dihydroisoquinolin-1(2H)-one | 5-fluoro-2-formyl pyridine histamine anhydrous THF | $^1$H NMR (300 MHz, CD$_3$OD) δ:2.83-2.98 (m, 1 H), 2.98-3.13 (m, 1 H), 3.17-3.26 (m, 1 H), 3.33-3.42 (m, 1 H), 3.49-3.62 (m, 1 H), 4.39 (ddd, J = 13.3, 7.5, 5.6 Hz, 1 H), 4.90 (d, J = 6.7 Hz, 1 H), 6.92 (s, 1 H), 7.20 (dd, J = 8.6, 4.2 Hz, 1 H), 7.32 (d, J = 8.2 Hz, 1 H), 7.45 (td, J = 8.6, 2.8 Hz, 1 H), 7.66 (s, 1 H), 8.20 (dd, J = 8.4, 2.5 Hz, 1 H), 8.28 (d, J = 2.9 Hz, 1 H), 8.75 (d, J = 2.6 Hz, 1 H) | brown-orange solid |
| 7 | 2-(2-(1H-imidazol-4-yl)ethyl)-3-(5-chlorofuran-2-yl)-7-nitro-3,4-dihydroisoquinolin-1(2H)-one | 5-chloro-2-furylaldehyde histamine anhydrous THF | $^1$H NMR (300 MHz, CD$_3$OD) δ: 2.86-3.12 (m, 3 H), 3.19-3.28 (m, 1 H), 3.35-3.49 (m, 1 H), 4.28-4.44 (m, 1 H), 4.80 (d, J = 4.4 Hz, 1 H), 6.08 (s, 2 H), 6.91 (s, 1 H), 7.51 (s, 1 H), 7.65 (s, 1 H), 8.31 (d, J = 5.9 Hz, 1 H), 8.75 (s, 1 H) | yellow-brown solid |
| 8 | 3-(6-chloropyridin-3-yl)-2-[2-(1H-imidazol-4-yl)ethyl]-7-nitro-3,4-dihydroisoquinolin-1(2H)-one | 6-chloropyridine carboxaldehyde histamine anhydrous THF | $^1$H NMR (300 MHz, CD$_3$OD) δ: 2.87-3.11 (m, 2 H), 3.17-3.29 (m, 2 H), 3.61 (dd, J = 16.4, 6.4 Hz, 1 H), 4.34 (dt, J = 13.2, 6.6 Hz, 1 H), 4.98 (d, J = 5.0 Hz, 1 H), 6.91 (s, 1 H), 7.26-7.33 (m, 1 H), 7.37 (d, J = 8.8 Hz, 1 H), 7.46 (dd, J = 8.4, 2.5 Hz, 1 H), 7.63 (s, 1 H), 8.13 (d, J = 2.3 Hz, 1 H), 8.27 (d, J = 8.2 Hz, 1 H), 8.79 (d, J = 2.3 Hz, 1 H) | orange solid |

TABLE 1-continued

| Interm. No. | IUPAC name | Reagent(s) Reactant(s) | $^1$H NMR δ (ppm) for Intermediate | Features |
|---|---|---|---|---|
| 9 | 3-(5-chloropyridin-2-yl)-2-[2-(1H-imidazol-4-yl)ethyl]-7-nitro-3,4-dihydroisoquinolin-1(2H)-one | 5-chloro-formylpyridine anhydrous CH$_3$CN histamine mW 130° C. 4 minutes | $^1$H NMR (600 MHz, CD$_3$OD) δ: 8.75 (d, J = 2.6 Hz, 1H), 8.37 (d, J = 2.6 Hz, 1H), 8.21 (dd, J = 8.4, 2.5 Hz, 1H), 7.64-7.72 (m, 2H), 7.32 (d, J = 8.5 Hz, 1H), 7.16 (d, J = 8.5 Hz, 1H), 6.92 (s, 1H), 4.90 (dd, J = 6.7, 1.8 Hz, 1H), 4.37-4.42 (m, 1H), 3.53-3.58 (m, 1H), 3.38 (dd, J = 16.6, 2.2 Hz, 1H), 3.24 (dt, J = 13.4, 7.5 Hz, 1H), 3.05 (dt, J = 14.7, 7.4 Hz, 1H), 2.89-2.95 (m, 1H) | brown-red solid |
| 10 | (S)-tert-butyl {3-[3-(4-cyanophenyl)-7-nitro-1-oxo-3,4-dihydroisoquinolin-2(1H)-yl]propyl}carbamate | chiral HPLC Intermediate 13 | $^1$H NMR (300 MHz, CD$_3$OD) δ: 8.80 (d, J = 2.3 Hz, 1H), 8.24 (dd, J = 8.2, 2.3 Hz, 1H), 7.63 (d, J = 8.2 Hz, 2H), 7.36 (d, J = 8.2 Hz, 1H), 7.30 (d, J = 8.2 Hz, 2H), 5.25 (d, J = 7.0 Hz, 1H), 4.10-4.25 (m, 1H), 3.85 (dd, J = 17.0, 6.4 Hz, 1H), 3.31-3.36 (m, 1H), 3.13-3.24 (m, 1H), 3.01-3.13 (m, 1H), 2.87-3.01 (m, 1H), 1.75-1.93 (m, 2H), 1.41 (s, 9H) | yellow solid >99% ee, $[α]_D$ = −47.1° (c = 1.32, CH$_2$Cl$_2$) Single crystal X-ray crystallography confirmed. |
| 11 | (R)-tert-butyl {3-[3-(4-cyanophenyl)-7-[({[4-(methylthio)phenyl]amino}carbonyl)amino]-1-oxo-3,4-dihydroisoquinolin-2(1H)-yl]propyl}carbamate | chiral HPLC Intermediate 13 | $^1$H NMR (300 MHz, CD$_3$OD) δ: 8.80 (s, 1H), 8.25 (d, J = 9.1 Hz, 1H), 7.63 (d, J = 7.0 Hz, 2H), 7.36 (d, J = 8.2 Hz, 1H), 7.30 (d, J = 7.6 Hz, 2H), 5.24 (d, J = 7.3 Hz, 1H), 4.10-4.22 (m, 1H), 3.85 (dd, J = 16.4, 7.3 Hz, 1H), 3.33-3.37 (m, 1H), 3.13-3.25 (m, 1H), 3.02-3.13 (m, 1H), 2.88-3.01 (m, 1H), 1.77-1.91 (m, 2H), 1.41 (s, 9H) | yellow solid >99% ee, $[α]_D$ = +47.0° c = 1.51, CH$_2$Cl$_2$) |
| 12 | tert-butyl [3-(3-methyl-7-nitro-1-oxo-3,4-dihydroisoquinolin-2(1H)-yl)propyl]carbamate | Acetaldehyde 1-boc-propylenediamine 7-nitro-1H-2-Benzopyran-1,3(4H)-dione (CAS 36795-25-2) | $^1$H NMR (CD$_3$OD) δ: 8.70 (d, J = 2.1 Hz, 1H), 8.33 (dd, J = 8.4, 2.2 Hz, 1H), 7.55 (d, J = 8.5 Hz, 1H), 3.92-4.12 (m, 2H), 3.46 (dd, J = 16.6, 6.0 Hz, 1H), 3.04-3.26 (m, 3H), 2.98 (d, J = 16.7 Hz, 1H), 1.78-1.94 (m, 2H), 1.43 (s, 9H), 1.17 (d, J = 6.4 Hz, 3H) | yellow oil |

Example 2

Intermediate 13 tert-butyl (3-(7-amino-3-(4-cyanophenyl)-1-oxo-3,4-dihydroisoquinolin-2(1H)-yl)propyl)carbamate To a solution of Intermediate 1 (350 mg, 0.78 mmol) in 20 mL of MeOH was added 10% Pd/C (40 mg). A balloon filled with hydrogen gas was attached, and the reaction was stirred at 25° C. for 12 hrs. The mixture was filtered through Celite pad and the solvent was evaporated. The residue was purified by medium pressure liquid chromatography on silica gel using ethyl acetate:hexane (8:2) to yield Intermediate 13 as a yellow solid.

$^1$H NMR (300 MHz, CD$_3$OD) δ: 7.52-7.70 (m, 2H), 7.18-7.37 (m, 3H), 6.69-6.86 (m, 2H), 4.97-5.14 (m, 1H), 3.50-3.74 (m, 1H), 3.00-3.24 (m, 1H), 2.78-2.98 (m, 4H), 1.69-1.88 (m, 2H), 1.41 (s, 9H).

Intermediates 14, 15, 16, 17, 18, 19, 20, 21 and 22 were prepared from the corresponding nitro intermediate in a similar manner to the procedure described in Example 2 for Intermediate 13. The reactants used and the results are described below in Table 2.

TABLE 2

| Interm. No. | IUPAC name | Nitro Interm. No. | $^1$HNMR δ (ppm) for Intermediate | Features |
|---|---|---|---|---|
| 14 | tert-butyl (2-(7-amino-3-(4-cyanophenyl)-1-oxo-3,4-dihydroisoquinolin-2(1H)-yl)ethyl)carbamate | 2 | $^1$H NMR (300 MHz, CD$_3$OD) δ: 7.55-7.63 (m, 2H), 7.29-7.35 (m, 1H), 7.21-7.29 (m, 2H), 6.68-6.82 (m, 2H), 4.98-5.09 (m, 1H), 4.12-4.28 (m, 1H), 4.02-4.15 (m, 2H), 3.60-3.76 (m, 1H), 2.79-3.01 (m, 2H), 1.38 (s, 9H) | yellow solid |
| 15 | 4-(2-(2-(1H-imidazol-4-yl)ethyl)-7-amino-1-oxo-1,2,3,4-tetrahydroisoquinolin-3-yl)benzonitrile | 3 | $^1$H NMR (300 MHz, CD$_3$OD) δ: 2.80-3.21 (m, 4 H), 3.34-3.43 (m, 1 H), 4.30 (ddd, J = 13.0, 7.6, 5.4 Hz, 1 H), 4.75-4.83 (m, 1 H), 6.71-6.75 (m, 2 H), 6.88 (s, 1 H), 7.20 (s, 1 H), 7.23 (s, 1 H), 7.32 (d, J = 1.8 Hz, 1 H), 7.56 (s, 1 H), 7.59 (s, 1 H), 7.61 (s, 1 H) | yellow-orange solid |
| 16 | tert-butyl (2-(7-amino-3-(4-cyanophenyl)-1-oxo-3,4-dihydroisoquinolin-2(1H)-yl)ethyl)(methyl)carbamate | 4 | $^1$H NMR (300 MHz, CD$_3$OD) δ: 1.34 (s, 9 H), 2.65-2.76 (m, 1 H), 2.94 (br. s., 3 H), 3.16-3.26 (m, 1 H), 3.52-3.92 (m, 2 H), 4.14-4.27 (m, 0 H), 4.41-4.57 (m, 1 H), 5.03-5.11 (m, 1 H), 6.69-6.81 (m, 2 H), 7.26 (s, 1 H), 7.29 (s, 1 H), 7.32 (br. s., 1 H), 7.59 (s, 1 H), 7.62 (s, 1 H) | yellow solid |
| 17 | 2-(2-(1H-imidazol-4-yl)ethyl)-7-amino-3-(3,4-dichlorophenyl)-3,4-dihydroisoquinolin-1(2H)-one | 5 | $^1$H NMR (300 MHz, CD$_3$OD) δ: 2.78-3.21 (m, 4 H), 3.32-3.43 (m, 1 H), 4.27 (ddd, J = 13.1, 7.5, 5.7 Hz, 1 H), 4.66-4.76 (m, 1 H), 6.72-6.80 (m, 2 H), 6.91-6.98 (m, 1 H), 6.98-7.06 (m, 1 H), 7.13-7.23 (m, 2H), 7.33 (d, J = 1.5 Hz, 1 H), 7.73-7.81 (m, 1 H) | yellow solid |
| 18 | 2-(2-(1H-imidazol-4-yl)ethyl)-7-amino-3-(5-fluoropyridin-2-yl)-3,4-dihydroisoquinolin-1(2H)-one | 6 | $^1$H NMR (300 MHz, CD$_3$OD) δ: 2.83-2.95 (m, 1 H), 2.96-3.09 (m, 2 H), 3.09-3.21 (m, 1 H), 3.24-3.29 (m, 1 H), 4.32-4.43 (m, 1 H), 4.70 (d, J = 5.9 Hz, 1 H), 6.67-6.77 (m, 2 H), 6.88 (s, 1 H), 7.03 (dd, J = 8.5, 4.4 Hz, 1 H), 7.29 (d, J = 1.8 Hz, 1 H), 7.40 (td, J = 8.6, 2.8 Hz, 1 H), 7.62 (s, 1 H), 8.33 (d, J = 2.9 Hz, 1 H) | yellow solid |

TABLE 2-continued

| Interm. No. | IUPAC name | Nitro Interm. No. | ¹HNMR δ (ppm) for Intermediate | Features |
|---|---|---|---|---|
| 19 | 7-amino-3-(2-furyl)-2-[2-(1H-imidazol-4-yl)ethyl]-3,4-dihydroisoquinolin-1(2H)-one | 7 | ¹H NMR (300 MHz, CD$_3$OD) δ: 2.80-3.06 (m, 3 H), 3.09-3.21 (m, 1 H), 3.23-3.29 (m, 1 H), 4.29 (ddd, J = 13.3, 7.8, 5.0 Hz, 1 H), 4.65 (d, J = 4.1 Hz, 1 H), 5.89 (d, J = 3.2 Hz, 1 H), 6.19 (dd, J = 3.2, 1.8 Hz, 1 H), 6.74-6.81 (m, 1 H), 6.87 (s, 1 H), 6.90 (s, 1 H), 7.27 (d, J = 2.3 Hz, 1 H), 7.32 (s, 1 H), 7.62 (s, 1H) | yellow solid |
| 20 | (S)-tert-butyl {3-[3-(4-cyanophenyl)-7-[({[4-(methylthio)phenyl]amino}carbonyl)amino]-1-oxo-3,4-dihydroisoquinolin-2(1H)-yl]propyl}carbamate | 10 | ¹H NMR (300 MHz, CD$_3$OD) δ: 7.60 (d, J = 8.2 Hz, 2H), 7.32 (d, J = 1.8 Hz, 1H), 7.26 (d, J = 7.9 Hz, 2H), 6.73-6.78 (m, 2H), 5.04 (d, J = 6.2 Hz, 1H), 4.02-4.16 (m, 1H), 3.60 (dd, J = 16.1, 6.2 Hz, 1H), 3.11-3.23 (m, 1H), 3.00-3.11 (m, 1H), 2.80-2.99 (m, 2H), 1.73-1.85 (m, 2H), 1.41 (s, 9H). | off-white solid $[\alpha]_D = -65.2°$ (c = 1.31, CH$_2$Cl$_2$). |
| 21 | (R)-tert-butyl {3-[3-(4-cyanophenyl)-7-[({[4-(methylthio)phenyl]amino}carbonyl)amino]-1-oxo-3,4-dihydroisoquinolin-2(1H)-yl]propyl}carbamate | 11 | ¹H NMR (300 MHz, CD$_3$OD) δ: 7.60 (d, J = 8.2 Hz, 2H), 7.32 (d, J = 2.1 Hz, 1H), 7.26 (d, J = 8.2 Hz, 2H), 6.70-6.83 (m, 2H), 5.04 (d, J = 6.7 Hz, 1H), 4.02-4.17 (m, 1H), 3.60 (dd, J = 16.3, 6.6 Hz, 1H), 3.10-3.24 (m, 1H), 3.00-3.10 (m, 1H), 2.80-3.00 (m, 2H), 1.72-1.87 (m, 2H), 1.41 (s, 9H). | white solid $[[\alpha]_D = +69.6°$ (c = 1.20, CH$_2$Cl$_2$) |
| 22 | tert-butyl [3-(7-amino-3-methyl-1-oxo-3,4-dihydroisoquinolin-2(1H)-yl)propyl]carbamate | 12 | ¹H NMR (CD$_3$OD) δ: 7.26 (d, J = 2.1 Hz, 1H), 6.99 (d, J = 8.2 Hz, 1H), 6.81-6.87 (m, 1H), 4.01 (dt, J = 13.7, 7.1 Hz, 1H), 3.77-3.85 (m, 1H), 3.21-3.28 (m, 1H), 3.12-3.21 (m, 1H), 2.97-3.10 (m, 2H), 2.62 (d, J = 15.2 Hz, 1H), 1.76-1.86 (m, 2H), 1.43 (s, 9H), 1.12 (d, J = 6.4 Hz, 2H). | light yellow solid |

Example 3

Intermediate 23 tert-butyl {3-[7-({[(4-acetylphenyl)amino]carbonyl}amino)-3-(4-cyanophenyl)-1-oxo-3,4-dihydroisoquinolin-2(1H)-yl]propyl}carbamate To a solution of Intermediate 13 (100 mg, 0.24 mmol) and 10 mL of anhydrous benzene under argon at 25° C. was added 4-acetylphenyl isocyanate (43 mg, 0.26 mmol) and triethylamine (50 mg, 0.48 mmol). The resulting mixture was heated to 100° C. for 12 hours and the reaction was quenched with water. The product was extracted with EtOAc, the layers were separated, and the organic layer was washed with brine, and dried over Na$_2$SO$_4$, and filtered, and concentrated under reduced pressure. The residue was purified by medium pressure liquid chromatography on silica gel using ethyl acetate:hexane (85:15) to yield Intermediate 23 as a light yellow solid.

¹H NMR (300 MHz, CD$_3$OD) δ: 7.88-8.10 (m, 3H), 7.52-7.70 (m, 5H), 7.22-7.35 (m, 2H), 6.95-7.11 (m, 1H), 5.08-5.22 (m, 1H), 4.06-4.26 (m, 1H), 3.61-3.81 (m, OH), 2.99-3.27 (m, 4H), 1.69-1.95 (m, 2H), 1.42 (s, 9H).

Intermediates 24, 25, 26, 27, 28, 29, 30 and 31 were prepared from the amino derivative in the presence of anhydrous benzene and the corresponding isocyanate in a similar manner to the procedure described in Example 3 for Intermediate 23. The reactants and reagents used and the results are described below in Table 3.

TABLE 3

| Interm. No. | IUPAC name | Reactant Reagent(s) | $^1$H NMR δ (ppm) for Intermediate | Features |
|---|---|---|---|---|
| 24 | tert-butyl {2-[7-({[(4-acetylphenyl)amino]carbonyl}amino)-3-(4-cyanophenyl)-1-oxo-3,4-dihydroisoquinolin-2(1H)-yl]ethyl}carbamate | Interm. 2 4-acetylphenyl isocyanate | $^1$H NMR (300 MHz, CD$_3$OD) δ: 7.98-8.05 (m, 1H), 7.95 (d, J = 8.8 Hz, 2H), 7.53-7.69 (m, 5H), 7.29 (d, J = 8.5 Hz, 2H), 6.96-7.07 (m, 1H), 5.05-5.22 (m, 1H), 4.13-4.34 (m, 1H), 3.67-3.86 (m, 1H), 3.35-3.45 (m, 1H), 3.01-3.16 (m, 1H), 2.82-3.00 (m, 1H), 2.56 (s, 3H), 1.39 (s, 9H) | yellow solid |
| 25 | tert-butyl {2-[7-({[(4-acetylphenyl)amino]carbonyl}amino)-3-(4-cyanophenyl)-1-oxo-3,4-dihydroisoquinolin-2(1H)-yl]ethyl}methylcarbamate. | Interm. 16 4-acetylphenyl isocyanate | $^1$HNMR (300 MHz, CD$_3$OD) δ: 1.34 (s, 9H), 2.55 (s, 3 H), 2.68-2.79 (m, 1 H), 2.95 (br. s., 3 H), 3.03-3.17 (m, 1 H), 3.62-3.96 (m, 2 H), 4.19-4.31 (m, 1 H), 4.47-4.62 (m, 1 H), 5.02 (br. s., 1 H), 5.14 (br. s., 1 H), 7.00 (br. s., 1 H), 7.29 (s, 1 H), 7.32 (s, 1 H), 7.54-7.66 (m, 5 H), 7.93 (s, 1 H), 7.96 (s, 1 H), 8.01 (br. s., 1 H) | yellow solid |
| 26 | tert-butyl {3-[3-(4-cyanophenyl)-1-oxo-7-[({[4-(trifluoromethyl)phenyl]amino}carbonyl)amino]-3,4-dihydroisoquinolin-2(1H)-yl]propyl}carbamate | Interm. 13 α,α,α-trifluoro-p-tolyl)-isocyanate | $^1$H NMR (300 MHz, CD$_3$OD) δ: 1.74-1.91 (m, 2 H), 2.84-2.98 (m, 1 H), 3.00-3.13 (m, 2H), 3.13-3.24 (m, 1 H), 3.70 (dd, J = 16.3, 6.6 Hz, 1 H), 4.06-4.19 (m, 1 H), 5.12 (d, J = 5.9 Hz, 1 H), 7.02 (d, J = 8.2 Hz, 1 H), 7.28 (d, J = 8.2 Hz, 2 H), 7.51-7.68 (m, 7 H), 8.01 (d, J = 2.3 Hz, 1 H) | white solid |
| 27 | tert-butyl {3-[3-(4-cyanophenyl)-7-[({[4-(methylthio)phenyl]amino}carbonyl)amino]-1-oxo-3,4-dihydroisoquinolin-2(1H)-yl]propyl}carbamate | Interm. 13 4-(methylthio)-phenyl isocyanate | $^1$H NMR (300 MHz, CD$_3$OD) δ: 1.41 (s, 9 H), 1.76-1.87 (m, 2 H), 2.90 (ddd, J = 14.2, 7.0, 6.9 Hz, 1 H), 3.00-3.12 (m, 2 H), 3.12-3.24 (m, 0 H), 3.69 (dd, J = 16.4, 6.4 Hz, 1 H), 4.12 (ddd, J = 14.0, 7.3, 7.1 Hz, 1 H), 5.11 (d, J = 5.9 Hz, 1 H), 7.00 (d, J = 8.2 Hz, 1 H), 7.20-7.31 (m, 3H), 7.34-7.37 (m, 2 H), 7.37-7.40 (m, 1 H), | white solid |

TABLE 3-continued

| Interm. No. | IUPAC name | Reactant Reagent(s) | $^1$H NMR δ (ppm) for Intermediate | Features |
|---|---|---|---|---|
| | | | 7.55 (d, J = 2.6 Hz, 1 H), 7.56-7.60 (m, 1 H), 7.62 (s, 1 H), 7.98 (d, J = 2.3 Hz, 1 H) | |
| 28 | tert-butyl {3-[7-({[(4-bromophenyl)amino]carbonyl}amino)-3-(4-cyanophenyl)-1-oxo-3,4-dihydroisoquinolin-2(1H)-yl]propyl}carbamate | Interm. 13 4-bromophenyl isocyanate | $^1$HNMR (300 MHz, CD$_3$OD) δ: 1.41 (s, 9H), 1.73-1.89 (m, 2H), 2.82-2.99 (m, 1 H), 2.99-3.13 (m, 2 H), 3.12-3.25 (m, 1 H), 3.69 (dd, J = 16.7, 6.4 Hz, 1 H), 4.04-4.21 (m, 1 H), 5.11 (d, J = 5.0 Hz, 1 H), 7.01 (d, J = 7.9 Hz, 1 H), 7.28 (d, J = 7.9 Hz, 2 H), 7.33-7.44 (m, 4 H), 7.52-7.65 (m, 3 H), 7.98 (d, J = 2.1 Hz, 1 H) | white solid |
| 29 | (S)-tert-butyl {3-[3-(4-cyanophenyl)-7-[({[4-(methylthio)phenyl]amino}carbonyl)amino]-1-oxo-3,4-dihydroisoquinolin-2(1H)-yl]propyl}carbamate | Interm. 20 4-(methylthio)-phenyl isocyanate | $^1$HNMR (300 MHz, CD$_3$OD) δ: 7.97 (d, 1H), 7.58-7.64 (m, 2H), 7.56 (d, J = 2.6 Hz, 1H), 7.37 (d, J = 8.8 Hz, 2H), 7.21-7.32 (m, 4H), 7.01 (d, J = 8.2 Hz, 1H), 5.11 (d, J = 6.4 Hz, 1H), 4.07-4.16 (m, 1H), 3.64-3.75 (m, 1H), 3.13-3.22 (m, 1H), 3.02-3.12 (m, 2H), 2.86-2.96 (m, 1H), 2.44 (s, 3H), 1.77-1.86 (m, 2H), 1.41 (s, 9H) | yellow solid $[α]_D$ = −55.9° (c = 0.72, CH$_2$Cl$_2$). |
| 30 | (R)-tert-butyl {3-[3-(4-cyanophenyl)-7-[({[4-(methylthio)phenyl]amino}carbonyl)amino]-1-oxo-3,4-dihydroisoquinolin-2(1H)-yl]propyl}carbamate | Interm. 21 4-(methylthio)-phenyl isocyanate | $^1$HNMR (300 MHz, CD$_3$OD) δ: 7.98 (s, 1H), 7.52-7.62 (m, 3H), 7.37 (d, J = 8.8 Hz, 2H), 7.25 (dd, J = 13.8, 8.2 Hz, 4H), 6.99 (d, J = 8.5 Hz, 1H), 5.10 (d, J = 5.3 Hz, 1H), 4.05-4.18 (m, 1H), 3.68 (dd, J = 16.1, 6.7 Hz, 1H), 3.12-3.24 (m, 1H), 3.00-3.12 (m, 2H), 2.83-2.96 (m, 1H), 2.43 (s, 3H), 1.75-1.87 (m, 2H), 1.41 (s, 9H) | yellow solid $[α]_D$ = +52.1° (c = 1.49, CH$_2$Cl$_2$) |

TABLE 3-continued

| Interm. No. | IUPAC name | Reactant Reagent(s) | $^1$H NMR δ (ppm) for Intermediate | Features |
|---|---|---|---|---|
| 31 | tert-butyl (3-{3-methyl-7-[({[4-(methylthio)phenyl]amino}carbonyl)amino]-1-oxo-3,4-dihydroisoquinolin-2(1H)-yl}propyl)carbamate | 4-(methylthio)phenyl isocyanate Triethylamine Interm. 22 | $^1$H NMR (CD$_3$OD) δ: 7.84 (d, J = 2.1 Hz, 1H), 7.70 (dd, J = 8.1, 2.2 Hz, 2H), 7.38 (d, J = 8.5 Hz, 2H), 7.18-7.27 (m, 3H), 4.03 (dt, J = 13.8, 7.2 Hz, 1H), 3.82-3.91 (m, 1H), 3.32-3.35 (m, 0H), 3.13-3.25 (m, 0H), 3.01-3.13 (m, 2H), 2.69-2.80 (m, 1H), 2.44 (s, 3H), 1.77-1.89 (m, 2H), 1.43 (s, 9H), 1.15 (d, 3H). | light yellow solid |

Example 4

Intermediate 32

7-amino-3-(5-chloro-2-furyl)-2-[2-(1H-imidazol-4-yl)ethyl]-3,4-dihydroisoquinolin-1(2H)-one To a solution of Intermediate 13 (445 mg, 1.15 mmol) in 20 mL of EtOH was added SnCl$_2$.2H$_2$O (1.04 g, 4.60 mmol). The mixture was heated to 80° C. for 3 hrs. The solvent was evaporated and the residue was purified by medium pressure liquid chromatography on silica gel using 10% 7N NH$_3$-MeOH:CH$_2$Cl$_2$ (80:20) to yield Intermediate 32 as a yellow solid.

$^1$H NMR (300 MHz, CD$_3$OD) δ: 2.81-3.06 (m, 3H), 3.12 (d, J=5.9 Hz, 1H), 3.21-3.28 (m, 1H), 4.25-4.39 (m, 1H), 4.63 (d, J=4.7 Hz, 1H), 5.93 (d, J=3.2 Hz, 1H), 6.04 (d, J=3.2 Hz, 1H), 6.75-6.84 (m, 1H), 6.86-6.96 (m, 2H), 7.27 (d, J=2.6 Hz, 1H), 7.66 (s, 1H).

Intermediates 33 and 34 were prepared from the corresponding nitro intermediate in the presence of SnCl$_2$.:2H$_2$O in a similar manner to the procedure described in Example 4 for Intermediate 32. The reactants and the results are described below in Table 4.

TABLE 4

| Interm. No. | IUPAC name | Nitro Interm No. | $^1$H NMR δ (ppm) for Intermediate | Features |
|---|---|---|---|---|
| 33 | 7-amino-3-(6-chloropyridin-3-yl)-2-[2-(1H-imidazol-4-yl)ethyl]-3,4-dihydroisoquinolin-1(2H)-one | 8 | $^1$H NMR (300 MHz, CD$_3$OD) δ: 2.80 (d, 1 H), 2.85-2.95 (m, 1 H), 2.94-3.07 (m, 1 H), 3.19 (ddd, J = 13.4, 7.8, 7.5 Hz, 1 H), 3.37 (dd, J = 15.7, 6.3 Hz, 1 H), 4.20-4.32 (m, 1 H), 4.78 (d, J = 6.7 Hz, 1 H), 6.72-6.81 (m, 2 H), 6.88 (s, 1 H), 7.24-7.30 (m, 1 H), 7.32 (d, J = 2.1 Hz, 1 H), 7.42 (dd, J = 8.4, 2.5 Hz, 1 H), 7.62 (s, 1 H), 8.06 (d, J = 2.6 Hz, 1 H) | yellow solid |
| 34 | 7-amino-3-(5-chloropyridin-2-yl)-2-[2-(1H-imidazol-4-yl)ethyl]-3,4-dihydroisoquinolin-1(2H)-one | 9 | $^1$H NMR (300 MHz, CD$_3$OD) δ: 8.42 (d, J = 2.3 Hz, 1H), 7.60-7.66 (m, 2H), 7.29 (d, J = 2.1 Hz, 1H), 7.00 (d, J = 8.2 Hz, 1H), 6.89 (s, 1H), 6.70-6.75 (m, 2H), 4.69 (d, J = 6.2 Hz, 1H), 4.32-4.46 (m, 1H), 3.20-3.28 (m, 1H), 3.15 (dd, J = 13.0, 7.2 Hz, 1H), 2.97-3.10 (m, 2H), 2.83-2.96 (m, 1H) | off-white solid |

Example 5

Intermediate 35 tert-butyl {3-[3-(4-cyanophenyl)-7-[({[4-(methyl-sulfinyl)phenyl]amino}carbonyl)amino]-1-oxo-3,4-dihydroisoquinolin-2(1H)-yl]propyl}carbamate To a solution of Intermediate 27 (62 mg, 0.11 mmol) and 10 mL of anhydrous THF at 0° C. was added meta-chloroperbenzoic acid (20 mg, 0.11 mmol). The mixture was stirred at 0° C. for 2 hours. The reaction was quenched with 2N $Na_2CO_3$ solution and product was extracted with EtOAc. The organic extracts were combined and washed with water, and brine, and dried over $Na_2SO_4$, and filtered, and concentrated under reduced pressure. The residue was purified by medium pressure liquid chromatography on silica gel using methanol:dichloromethane (1:9) to yield Intermediate 35 as a white solid.

$^1$H NMR (300 MHz, $CD_3OD$) δ: 1.42 (s, 9H), 1.75-1.90 (m, 2H), 2.79 (s, 3H), 2.84-2.98 (m, 1H), 3.00-3.13 (m, 2H), 3.13-3.25 (m, 1H), 3.70 (dd, J=15.8, 7.0 Hz, 1H), 4.05-4.19 (m, 1H), 5.12 (d, J=6.2 Hz, 1H), 7.02 (d, J=8.2 Hz, 1H), 7.29 (d, J=8.2 Hz, 2H), 7.53-7.75 (m, 7H), 8.02 (d, J=2.3 Hz, 1H).

Intermediates 36, 37 and 38 were prepared from the thio derivative in the presence of meta-chloroperbenzoic acid in a similar manner to the procedure described in Example 5 for Intermediate 35. Using 5.0 equivalents of meta-chloroperbenzoic acid in the procedure of Example 5 and stirring the reaction mixture at 25° C. for 0.5 h lead to the sulfonyl derivatives Intermediate 39 and 40. The reactant used and the results are described below in Table 5.

TABLE 5

| Interm. No. | IUPAC name | Thio Interm. No. | $^1$H NMR δ (ppm) for Intermediate | Features |
|---|---|---|---|---|
| 36 | (S)-1-[2-(3-aminopropyl)-3-(4-cyanophenyl)-1-oxo-1,2,3,4-tetrahydroisoquinolin-7-yl]-3-[4-methylsulfinyl)phenyl]urea | 29 | $^1$H NMR (300 MHz, $CD_3OD$) δ: 8.03 (d, J = 1.8 Hz, 1H), 7.53-7.73 (m, 7H), 7.27 (d, J = 8.2 Hz, 2H), 7.00 (d, J = 8.2 Hz, 1H), 5.11 (d, J = 5.6 Hz, 1H), 4.06-4.19 (m, 1H), 3.69 (dd, J = 16.0, 6.6 Hz, 1H), 3.13-3.24 (m, 1H), 3.00-3.12 (m, 2H), 2.84-2.97 (m, 1H), 2.78 (s, 3H), 1.75-1.90 (m, 2H), 1.41 (s, 9H). | white solid |
| 37 | (R)-1-[2-(3-aminopropyl)-3-(4-cyanophenyl)-1-oxo-1,2,3,4-tetrahydroisoquinolin-7-yl]-3-[4-(methylsulfinyl)phenyl]urea. | 30 | $^1$H NMR (300 MHz, $CD_3OD$) δ: 8.03 (d, J = 1.8 Hz, 1H), 7.53-7.73 (m, 7H), 7.27 (d, J = 8.2 Hz, 2H), 7.00 (d, J = 8.2 Hz, 1H), 5.11 (d, J = 5.6 Hz, 1H), 4.06-4.19 (m, 1H), 3.69 (dd, J = 16.0, 6.6 Hz, 1H), 3.13-3.24 (m, 1H), 3.00-3.12 (m, 2H), 2.84-2.97 (m, 1H), 2.78 (s, 3H), 1.75-1.90 (m, 2H), 1.41 (s, 9H). | white solid $[α]_D = +77.2°$ (c = 0.64, $CH_2Cl_2$). |
| 38 | (S)-tert-butyl {3-[3-(4-cyanophenyl)-7-[({[4-(methylsulfonyl)phenyl]amino}carbonyl)amino]-1-oxo-3,4-dihydroisoquinolin-2(1H)-yl]propyl}carbamate | 30 | $^1$H NMR ($CD_3OD$) δ: 8.03 (d, J = 2.1 Hz, 1H), 7.85 (d, J = 8.8 Hz, 2H), 7.70 (d, J = 8.8 Hz, 2H), 7.54-7.64 (m, 3H), 7.28 (d, J = 7.9 Hz, 2H), 7.02 (d, J = 8.2 Hz, 1H), 5.12 (d, J = 6.4 Hz, 1H), 4.07-4.19 (m, 1H), 3.70 (dd, J = 16.1, 7.0 Hz, 1H), 3.14-3.24 (m, 1H), 3.09 (s, 3H), 3.05-3.13 (m, 2H), 2.84-2.96 (m, 1H), 1.77-1.89 (m, 2H), 1.41 (s, 9H). | white solid $[α]_D = -62.1°$ (c = 1.14, $CH_2Cl_2$). |

TABLE 5-continued

| Interm. No. | IUPAC name | Thio Interm. No. | ¹H NMR δ (ppm) for Intermediate | Features |
|---|---|---|---|---|
| 39 | tert-butyl {3-[3-(4-cyanophenyl)-7-[({[4-(methylsulfonyl)phenyl]amino}carbonyl)amino]-1-oxo-3,4-dihydroisoquinolin-2(1H)-yl]propyl}carbamate | 27 | ¹H NMR (300 MHz, CD$_3$OD) δ: 1.42 (s, 9 H), 1.76-1.88 (m, 2 H), 2.85-3.07 (m, 2 H), 3.09 (s, 3 H), 3.10-3.23 (m, 2 H), 3.70 (dd, J = 16.8, 6.6 Hz, 1 H), 4.06-4.19 (m, 1 H), 5.12 (d, J = 7.0 Hz, 1 H), 7.03 (d, J = 8.2 Hz, 1 H), 7.29 (d, J = 8.2 Hz, 2 H), 7.57 (d, J = 2.3 Hz, 1 H), 7.60 (s, 1 H), 7.62-7.64 (m, 1 H), 7.66-7.75 (m, 2 H), 7.85 (q, J = 4.7 Hz, 1 H), 8.03 (d, J = 2.3 Hz, 1 H). | yellow solid |
| 40 | (R)-tert-butyl {3-[3-(4-cyanophenyl)-7-[({[4-(methylsulfonyl)phenyl]amino}carbonyl)amino]-1-oxo-3,4-dihydroisoquinolin-2(1H).yl]propyl}carbamate | 30 | ¹H NMR (CD$_3$OD) δ: 8.03 (d, J = 2.1 Hz, 1H), 7.85 (d, J = 8.8 Hz, 2H), 7.70 (d, J = 8.8 Hz, 2H), 7.54-7.64 (m, 3H), 7.28 (d, J = 7.9 Hz, 2H), 7.02 (d, J = 8.2 Hz, 1H), 5.12 (d, J = 6.4 Hz, 1H), 4.07-4.19 (m, 1H), 3.70 (dd, J = 16.1, 7.0 Hz, 1H), 3.14-3.24 (m, 1H), 3.09 (s, 3H), 3.05-3.13 (m, 2H), 2.84-2.96 (m, 1H), 1.77-1.89 (m, 2H), 1.41 (s, 9H). | white solid [[α]]$_D$ = +63.3° (c = 1.16, CH$_2$Cl$_2$). |
| 41 | tert-butyl (3-{3-methyl-7-[({[4-(methylsulfonyl)phenyl]amino}carbonyl)amino]-1-oxo-3,4-dihydroisoquinolin-2(1H).yl}propyl)carbamate | 31 | ¹H NMR (CD$_3$OD) δ: 7.90 (d, J = 2.1 Hz, 1H), 7.84 (d, J = 8.5 Hz, 2H), 7.69 (d, J = 8.5 Hz, 3H), 7.21 (d, J = 8.2 Hz, 1H), 4.03 (dt, J = 13.8, 7.0 Hz, 1H), 3.82-3.91 (m, 1H), 3.31 (s, 3H), 3.24-3.29 (m, 1H), 3.13-3.22 (m, 1H), 3.01-3.07 (m, 2H), 2.73 (d, J = 16.1 Hz, 1H), 1.77-1.89 (m, 2H), 1.43 (s, 9H), 1.14 (d, 3H). | |

43

Example 6

Intermediate 42 tert-butyl {3-[3-(4-cyanophenyl)-7-[({[4-(ethylthio)phenyl]amino}carbonyl)amino]-1-oxo-3,4-dihydroisoquinolin-2(1H-yl]propyl}carbamate In a sealed tube, a solution of Compound 6 (85 mg, 0.14 mmol) and 8 mL of 1,4-dioxane was purged under argon at 25° C. and ethanethiol (0.05 ml, 0.70 mmol), $Pd_2(dba)_3$ (12 mg, 0.014 mmol), Xantphos (16 mg, 0.028 mmol) and diisopropylethylamine (0.1 mL, 0.0.56 mmol) were added. The resulting mixture was heated to 110° C. for 12 hours. The mixture was concentrated and the residue was purified by medium pressure liquid chromatography on silica gel using ethyl acetate:hexane (7:3) to yield Intermediate 42 as a yellow solid.

$^1$H NMR (600 MHz, $CD_3OD$) δ: 7.98 (d, J=2.3 Hz, 1H), 7.61 (d, J=8.5 Hz, 2H), 7.57 (dd, J=8.2, 2.3 Hz, 1H), 7.34-7.41 (m, 2H), 7.24-7.33 (m, 4H), 7.00 (d, J=8.2 Hz, 1H), 5.11 (d, J=6.2 Hz, 1H), 4.12 (td, J=13.4, 7.2 Hz, 1H), 3.69 (dd, J=16.1, 6.5 Hz, 1H), 3.15-3.24 (m, 1H), 3.02-3.11 (m, 2H), 2.89-2.93 (m, 1H), 2.87 (q, J=7.3 Hz, 2H), 1.76-1.88 (m, 2H), 1.42 (s, 9H), 1.20-1.27 (m, 3H).

Example 7

Compound 1

1-(4-acetylphenyl)-3-[2-(3-aminopropyl)-3-(4-cyanophenyl)-1-oxo-1,2,3,4-tetrahydroisoquinolin-7-yl]urea

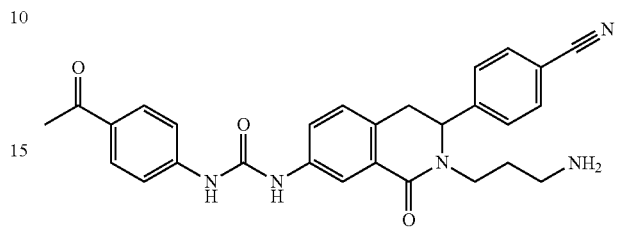

To a solution of Intermediate 23 (75 mg, 0.13 mmol) and 4 mL of anhydrous $CH_2Cl_2$ under argon at 25° C. was added TFA (0.2 mL). The resulting mixture was stirred for 2 hours and the reaction was quenched by the addition of 7N $NH_3$-MeOH (0.2 mL) at 0° C. Silica gel (100 mg) was added and the mixture was concentrated to dryness. The resulting product was purified by medium pressure liquid chromatography on silica gel using an eluent of 10% 7N $NH_3$-MeOH:$CH_2Cl_2$ (80:20) to yield Compound 1 as a light yellow solid.

$^1$H NMR (300 MHz, $CD_3OD$) δ: $^1$H NMR ($CD_3OD$) δ: 7.88-8.10 (m, 3H), 7.52-7.70 (m, 5H), 7.22-7.35 (m, 2H), 6.95-7.11 (m, 1H), 5.08-5.22 (m, 1H), 4.06-4.26 (m, 1H), 3.61-3.81 (m, OH), 2.99-3.27 (m, 4H), 1.69-1.95 (m, 2H), 1.42 (s, 9H).

Compounds 2, 3, 4, 5, 6, 7, 8, 9, 10, 11, 12, 13, 14, 15, 16 and 17 were prepared from the amino intermediate derivative in the presence of trifluoroacetic acid and the corresponding protected amine in a similar manner to the procedure described in Example 7 for Compound 1. The intermediate used and the results are described below in Table 6.

TABLE 6

| Comp No. | IUPAC name | Amino. Interm | $^1$H NMR δ (ppm) for Compound | Features |
|---|---|---|---|---|
| 2 | 1-(4-acetylphenyl)-3-[2-(2-aminoethyl)-3-(4-cyanophenyl)-1-oxo-1,2,3,4-tetrahydroisoquinolin-7-yl]urea | 24 | $^1$H NMR (300 MHz, $CD_3OD$) δ: 8.05 (d, J = 2.3 Hz, 1H), 7.94 (d, J = 8.5 Hz, 2H), 7.49-7.67 (m, 5H), 7.29 (d, J = 8.5 Hz, 2H), 7.02 (d, J = 8.2 Hz, 1H), 5.06-5.20 (m, 1H), 4.06-4.26 (m, 1H), 3.67-3.86 (m, 1H), 3.01-3.15 (m, 1H), 2.83-3.01 (m, 3H), 2.55 (s, 3H). | white solid |

TABLE 6-continued

| Comp No. | IUPAC name | Amino. Interm | ¹H NMR δ (ppm) for Compound | Features |
|---|---|---|---|---|
| 3 | 1-(4-acetylphenyl)-3-{3-(4-cyanophenyl)-2-[2-(methylamino)ethyl]-1-oxo-1,2,3,4-tetrahydroisoquinolin-7-yl}urea | 25 | ¹H NMR (CD₃OD) δ: 2.41 (s, 3 H), 2.55 (s, 3 H), 2.81-2.90 (m, 2 H), 2.93-3.12 (m, 2 H), 3.75 (dd, J = 16.0, 6.9 Hz, 1 H), 4.24 (ddd, J = 13.4, 7.0, 6.8 Hz, 1 H), 5.13 (d, J = 5.9 Hz, 1 H), 7.01 (d, J = 8.2 Hz, 1 H), 7.27 (s, 1 H), 7.30 (s, 1 H), 7.53-7.64 (m, 5 H), 7.93 (s, 1 H), 7.95 (s, 1 H), 8.04 (d, J = 2.3 Hz, 1 H) | white solid |
| 4 | 1-[2-(3-aminopropyl)-3-(4-cyanophenyl)-1-oxo-1,2,3,4-tetrahydroisoquinolin-7-yl]-3-[4-(trifluoromethyl)phenyl]urea | 26 | ¹H NMR (CD₃OD) δ: 1.70-1.93 (m, 2 H), 2.70 (t, J = 6.3 Hz, 2 H), 2.96 (dt, J = 13.4, 6.6 Hz, 1 H), 3.08 (d, J = 16.1 Hz, 1 H), 3.65 (dd, J = 16.0, 6.3 Hz, 1 H), 4.09-4.25 (m, 1 H), 5.10 (d, J = 5.9 Hz, 1 H), 7.00 (d, J = 8.2 Hz, 1 H), 7.29 (d, J = 8.5 Hz, 2 H), 7.51-7.67 (m, 7 H), 8.04 (d, J = 2.1 Hz, 1 H) | white solid |
| 5 | 1-[2-(3-aminopropyl)-3-(4-cyanophenyl)-1-oxo-1,2,3,4-tetrahydroisoquinolin-7-yl]-3-[4-(methylthio)phenyl]urea | 27 | ¹H NMR (CD₃OD) δ: 1.72-1.88 (m, 1 H), 1.89-2.03 (m, 1 H), 2.43 (s, 3 H), 2.70 (t, J = 7.3 Hz, 1 H), 2.88-3.02 (m, 1 H), 3.07 (d, J = 16.1 Hz, 1 H), 3.24-3.29 (m, 1 H), 3.65 (dd, J = 15.8, 11.1 Hz, 1 H), 4.02-4.25 (m, 1 H), 5.12 (d, J = 7.9 Hz, 1 H), 6.99 (d, J = 8.2 Hz, 1 H), 7.19-7.32 (m, 4 H), 7.33-7.42 (m, 2 H), 7.50-7.64 (m, 3 H), 8.00 (d, J = 2.6 Hz, 1 H) | yellow solid |

TABLE 6-continued

| Comp No. | IUPAC name | Amino. Interm | ¹H NMR δ (ppm) for Compound | Features |
|---|---|---|---|---|
| 6 | 1-[2-(3-aminopropyl)-3-(4-cyanophenyl)-1-oxo-1,2,3,4-tetrahydroisoquinolin-7-yl]-3-(4-bromophenyl)urea | 28 | ¹H NMR (CD₃OD) δ: 1.75-1.92 (m, 2 H), 2.71 (t, J = 7.6 Hz, 2 H), 2.90-3.02 (m, 1 H), 3.08 (d, J = 16.1 Hz, 1 H), 3.66 (dd, J = 15.8, 6.7 Hz, 1 H), 4.10-4.27 (m, 0 H), 5.10 (d, J = 5.3 Hz, 1 H), 7.00 (d, J = 8.2 Hz, 1 H), 7.29 (d, J = 8.8 Hz, 2 H), 7.33-7.45 (m, 4 H), 7.55 (dd, J = 8.2, 2.3 Hz, 1 H), 7.59 (s, 1 H), 7.62 (s, 1 H), 8.01 (d, J = 2.3 Hz, 1 H) | white solid |
| 7 | 1-[2-(3-aminopropyl)-3-(4-cyanophenyl)-1-oxo-1,2,3,4-tetrahydroisoquinolin-7-yl]-3-[4-(methylsulfinyl)phenyl]urea | 35 | ¹H NMR (CD₃OD) δ: 1.76-1.98 (m, 2 H), 2.71-2.77 (m, 1 H), 2.92-3.04 (m, 1 H), 3.09 (dd, J = 16.0, 1.6 Hz, 1 H), 3.67 (dd, J = 16.0, 6.6 Hz, 1 H), 4.10-4.26 (m, 1 H), 5.11 (d, J = 5.3 Hz, 1 H), 7.02 (d, J = 8.2 Hz, 1 H), 7.30 (d, J = 8.5 Hz, 2 H), 7.55 (dd, J = 8.2, 2.3 Hz, 1 H), 7.58-7.74 (m, 6 H), 8.07 (d, J = 2.3 Hz, 1 H) | white solid |
| 8 | 1-[2-(3-aminopropyl)-3-(4-cyanophenyl)-1-oxo-1,2,3,4-tetrahydroisoquinolin-7-yl]-3-[4-(methylsulfonyl)phenyl]urea | 39 | ¹H NMR (CD₃OD) δ: 1.75-1.95 (m, 2 H), 2.75 (td, J = 6.9, 2.1 Hz, 2 H), 2.98 (m, 1 H), 3.09 (s, 3 H), 3.11-3.14 (m, 1 H), 3.67 (dd, J = 15.5, 6.7 Hz, 1 H), 4.10-4.26 (m, 1 H), 5.12 (d, J = 5.3 Hz, 1 H), 7.02 (d, J = 8.2 Hz, 1 H), 7.29 (d, J = 8.2 Hz, 2 H), 7.50-7.66 (m, 3 H), 7.66-7.75 (m, 2 H), 7.81-7.92 (m, 2 H), 8.07 (d, J = 2.3 Hz, 1 H) | white solid |

TABLE 6-continued

| Comp No. | IUPAC name | Amino. Interm | ¹H NMR δ (ppm) for Compound | Features |
|---|---|---|---|---|
| 9 | 1-[2-(3-aminopropyl)-3-(4-cyanophenyl)-1-oxo-1,2,3,4-tetrahydroisoquinolin-7-yl]-3-[4-(ethylthio)phenyl]urea | 42 | ¹H NMR (300 MHz, CD₃OD) δ: 8.00 (d, J = 1.5 Hz, 1H), 7.51-7.66 (m, 3H), 7.34-7.43 (m, 2H), 7.29 (dd, J = 8.4, 2.5 Hz, 4H), 6.99 (d, J = 8.2 Hz, 1H), 5.10 (d, J = 5.9 Hz, 1H), 4.07-4.25 (m, 1H), 3.65 (dd, J = 16.1, 6.4 Hz, 1H), 3.07 (d, J = 16.1 Hz, 1H), 2.79-3.01 (m, 3H), 2.70 (t, J = 6.4 Hz, 1H), 1.74-1.91 (m, 2H), 1.14-1.34 (m, 3H) | white solid |
| 10 | (S)-1-[2-(3-aminopropyl)-3-(4-cyanophenyl)-1-oxo-1,2,3,4-tetrahydroisoquinolin-7-yl]-3-[4-(methylthio)phenyl]urea | 29 | ¹H NMR (CD₃OD) δ: 8.13 (s, 1H), 7.62 (d, J = 7.3 Hz, 2H), 7.48 (d, J = 8.5 Hz, 1H), 7.39 (d, J = 7.6 Hz, 2H), 7.30 (d, J = 7.3 Hz, 2H), 7.23 (d, J = 7.3 Hz, 2H), 7.01 (d, J = 7.9 Hz, 1H), 5.16 (d, J = 6.7 Hz, 1H), 4.07-4.22 (m, 1H), 3.70 (dd, J = 15.7, 7.2 Hz, 1H), 2.88-3.14 (m, 4H), 2.44 (s, 3H), 1.91-2.12 (m, 2H) | white solid [α]_D = −71.7° (c = 1.09, CH₂Cl₂) |
| 11 | (R)-1-[2-(3-aminopropyl)-3-(4-cyanophenyl)-1-oxo-1,2,3,4-tetrahydroisoquinolin-7-yl]-3-[4-(methylthio)phenyl]urea | 30 | ¹H NMR (CD₃OD) δ: 8.13 (d, J = 2.1 Hz, 1H), 7.61 (d, J = 8.2 Hz, 2H), 7.47 (dd, J = 8.2, 2.1 Hz, 1H), 7.39 (d, J = 8.5 Hz, 2H), 7.29 (d, J = 8.2 Hz, 2H), 7.20-7.26 (m, 2H), 7.00 (d, J = 8.2 Hz, 1H), 5.14 (d, J = 5.9 Hz, 1H), 4.07-4.20 (m, 1H), 3.69 (dd, J = 16.1, 6.7 Hz, 1H), 2.88-3.14 (m, 4H), 2.43 (s, 3H), 1.89-2.09 (m, 2H) | white solid [α]_D = +77.4° (c = 1.33, CH₂Cl₂) |
| 12 | (S)-1-[2-(3-aminopropyl)-3-(4-cyanophenyl)-1-oxo-1,2,3,4-tetrahydroisoquinolin-7-yl]-3-[4-(methylsulfinyl)phenyl]urea | 36 | ¹H NMR (CD₃OD) δ: 8.13 (d, J = 2.1 Hz, 1H), 7.61 (d, J = 8.2 Hz, 2H), 7.47 (dd, J = 8.2, 2.1 Hz, 1H), 7.39 (d, J = 8.5 Hz, 2H), 7.29 (d, J = 8.2 Hz, 2H), 7.20-7.26 (m, 2H), 7.00 (d, J = 8.2 Hz, 1H), 5.14 (d, J = 5.9 Hz, 1H), 4.07-4.20 (m, 1H), 3.69 (dd, J = 16.1, 6.7 Hz, 1H), 2.88-3.14 (m, 4H), 2.43 (s, 3H), 1.89-2.09 (m, 2H) | white solid [α]_D = −57.9° (c = 1.03, CH₂Cl₂) |

TABLE 6-continued

| Comp No. | IUPAC name | Amino. Interm | $^1$H NMR δ (ppm) for Compound | Features |
|---|---|---|---|---|
| 13 | (S)-1-[2-(3-aminopropyl)-3-(4-cyanophenyl)-1-oxo-1,2,3,4-tetrahydroisoquinolin-7-yl]-3-[4-(methylsulfinyl)phenyl]urea | 37 | $^1$H NMR (CD$_3$OD) δ: 8.17 (d, J = 2.1 Hz, 1H), 7.60-7.74 (m, 6H), 7.49 (dd, J = 8.2, 2.3 Hz, 1H), 7.31 (d, J = 8.2 Hz, 2H), 7.04 (d, J = 7.9 Hz, 1H), 5.16 (d, J = 7.3 Hz, 1H), 4.07-4.20 (m, 1H), 3.72 (dd, J = 16.0, 7.2 Hz, 1H), 2.95-3.16 (m, 4H), 2.79 (s, 3H), 1.93-2.12 (m, 2H) | white solid $[α]_D$ = +63.3° (c = 1.16, CH$_2$Cl$_2$) |
| 14 | (S)-1-[2-(3-aminopropyl)-3-(4-cyanophenyl)-1-oxo-1,2,3,4-tetrahydroisoquinolin-7-yl]-3-[4-(methylsulfonyl)phenyl]urea | 38 | $^1$H NMR (CD$_3$OD) δ: 8.18 (d, J = 2.1 Hz, 1H), 7.85 (d, J = 8.8 Hz, 2H), 7.68-7.76 (m, 2H), 7.63 (d, J = 8.2 Hz, 2H), 7.51 (dd, J = 8.2, 2.3 Hz, 1H), 7.31 (d, J = 8.2 Hz, 2H), 7.04 (d, J = 8.2 Hz, 1H), 5.17 (d, J = 7.0 Hz, 1H), 4.07-4.21 (m, 2H), 3.73 (dd, J = 16.6, 5.4 Hz, 1H), 3.11-3.15 (m, 1H), 3.09 (s, 3H), 2.96-3.06 (m, 3H), 1.95-2.12 (m, 2H) | white solid $[α]_D$ = −53.6° (c = 0.89, CH$_2$Cl$_2$) |
| 15 | (R)-1-[2-(3-aminopropyl)-3-(4-cyanophenyl)-1-oxo-1,2,3,4-tetrahydroisoquinolin-7-yl]-3-[4-(methylsulfonyl)phenyl]urea | 40 | $^1$H NMR (CD$_3$OD) δ: 8.18 (d, J = 2.1 Hz, 1H), 7.85 (d, J = 8.8 Hz, 2H), 7.68-7.76 (m, 2H), 7.63 (d, J = 8.2 Hz, 2H), 7.51 (dd, J = 8.2, 2.3 Hz, 1H), 7.31 (d, J = 8.2 Hz, 2H), 7.04 (d, J = 8.2 Hz, 1H), 5.17 (d, J = 7.0 Hz, 1H), 4.07-4.21 (m, 2H), 3.73 (dd, J = 16.6, 5.4 Hz, 1H), 3.11-3.15 (m, 1H), 3.09 (s, 3H), 2.96-3.06 (m, 3H), 1.95-2.12 (m, 2H) | white solid $[α]_D$ = +50.5° (c = 0.61, CH$_2$Cl$_2$) |
| 16 | 1-[2-(3-aminopropyl)-3-methyl-1-oxo-1,2,3,4-tetrahydroisoquinolin-7-yl]-3-[4-(methylthio)phenyl]urea | 31 | $^1$H NMR (CD$_3$OD) δ: 7.90 (s, 1H), 7.66 (d, J = 7.9 Hz, 1H), 7.38 (d, J = 8.5 Hz, 2H), 7.17-7.28 (m, 3H), 4.06 (dt, J = 14.0, 7.2 Hz, 1H), 3.83-3.91 (m, 1H), 3.22-3.28 (m, 1H), 3.15 (dt, J = 13.3, 6.4 Hz, 1H), 2.69-2.81 (m, 3H), 1.82-1.94 (m, 2H), 1.15 (d, J = 6.4 Hz, 3H). | light yellow solid |

TABLE 6-continued

| Comp. No. | IUPAC name | Amino. Interm | $^1$H NMR δ (ppm) for Compound | Features |
|---|---|---|---|---|
| 17 | 1-[2-(3-aminopropyl)-3-methyl-1-oxo-1,2,3,4-tetrahydroisoquinolin-7-yl]-3-[4-(methylsulfonyl)phenyl]urea | 41 | $^1$H NMR (CD$_3$OD) δ: 8.03 (d, J = 2.1 Hz, 1H), 7.86 (d, J = 9.1 Hz, 2H), 7.72 (d, J = 9.1 Hz, 2H), 7.63 (d, J = 7.9 Hz, 1H), 7.25 (d, J = 7.9 Hz, 1H), 3.98-4.12 (m, 1H), 3.83-3.95 (m, 1H), 3.30 (s, 3H), 3.20-3.29 (m, 1H), 2.88-2.99 (m, 2H), 2.71-2.83 (m, 2H), 1.95-2.06 (m, 2H), 1.18 (d, J = 6.7 Hz, 6H). | |

Compounds 18, 19, 20, 21, 22, 23, 24, 25, 26, 27 and 28 were prepared from the amino intermediate derivative in the presence of anhydrous benzene and the corresponding isocyanate in a similar manner to the procedure described in Example 3 for Intermediate 23. The reactants and reagents used and the results are described below in Table 7.

TABLE 7

| Comp. No. | IUPAC name | Reactants | $^1$H NMR δ (ppm) for Compound | Features |
|---|---|---|---|---|
| 18 | 1-(4-acetylphenyl)-3-{3-(4-cyanophenyl)-2-[2-(1H-imidazol-4-yl)ethyl]-1-oxo-1,2,3,4-tetrahydroisoquinolin-7-yl}urea | Interm. 15 4-acetylphenyl isocyanate | $^1$H NMR (300 MHz, CD$_3$OD) δ: 2.56 (s, 3 H), 2.84-3.25 (m, 3 H), 3.41-3.56 (m, 1 H), 4.28-4.40 (m, 1 H), 4.86-4.90 (m, 1 H), 6.89 (s, 1 H), 6.99 (d, J = 8.5 Hz, 1 H), 7.23 (s, 1 H), 7.54-7.64 (m, 6 H), 7.92-7.95 (m, 1 H), 7.95-7.98 (m, 1 H), 8.01 (d, J = 2.3 Hz, 1 H) | white solid |
| 19 | 1-{3-(4-cyanophenyl)-2-[2-(1H-imidazol-4-yl)ethyl]-1-oxo-1,2,3,4-tetrahydroisoquinolin-7-yl}-3-[4-(trifluoromethyl)phenyl]urea | Interm. 15 α,α,α-trifluoro-p-tolyl)-isocyanate | $^1$H NMR (300 MHz, CD$_3$OD) δ: 2.83-3.23 (m, 4 H), 3.46 (dd, J = 16.1, 7.0 Hz, 1 H), 4.34 (ddd, J = 13.0, 7.5, 5.3 Hz, 1 H), 4.90 (s, 1 H), 6.89 (s, 1 H), 6.98 (d, J = 8.2 Hz, 1 H), 7.22 (s, 1 H), 7.25 (s, 1 H), 7.50-7.66 (m, 8 H), 8.02 (d, J = 2.3 Hz, 1 H) | yellow solid |

TABLE 7-continued

| Comp. No. | IUPAC name | Reactants | ¹H NMR δ (ppm) for Compound | Features |
|---|---|---|---|---|
| 20 | 1-(4-acetylphenyl)-3-{3-(3,4-dichlorophenyl)-2-[2-(1H-imidazol-4-yl)ethyl]-1-oxo-1,2,3,4-tetrahydroisoquinolin-7-yl}urea | Interm. 17 4-acetylphenyl isocyanate | ¹H NMR (300 MHz, CD₃OD) δ: 2.55 (s, 3 H), 2.84-3.22 (m, 4 H), 3.44 (dd, J = 15.8, 7.0 Hz, 1 H), 4.26-4.38 (m, 1 H), 4.76 (d, J = 5.0 Hz, 1 H), 6.91 (s, 1 H), 6.98 (d, J = 8.2 Hz, 1 H), 7.04 (d, J = 6.2 Hz, 2 H), 7.14-7.25 (m, 2 H), 7.57 (d, J = 8.5 Hz, 2 H), 7.69 (s, 1 H), 7.93 (s, 1 H), 7.96 (s, 1 H), 8.01 (d, J = 2.3 Hz, 1 H) | yellow solid |
| 21 | 1-{3-(4-cyanophenyl)-2-[2-(1H-imidazol-4-yl)ethyl]-1-oxo-1,2,3,4-tetrahydroisoquinolin-7-yl}-3-[4-(methylthio)phenyl]urea | Interm. 15 4-(methylthio)phenyl isocyanate | ¹H NMR (300 MHz, CD₃OD) δ: 2.43 (s, 3 H), 2.82-3.21 (m, 4 H), 3.45 (dd, J = 16.0, 6.6 Hz, 1 H), 4.27-4.39 (m, 1 H), 4.86-4.90 (m, 1 H), 6.89 (s, 1 H), 6.96 (d, J = 8.5 Hz, 1 H), 7.20-7.27 (m, 4 H), 7.36 (s, 1 H), 7.39 (s, 1 H), 7.50-7.64 (m, 4 H), 7.97 (d, J = 2.1 Hz, 1 H) | white solid |
| 22 | 1-{3-(6-fluoropyridin-3-yl)-2-[2-(1H-imidazol-4-yl)ethyl]-1-oxo-1,2,3,4-tetrahydroisoquinolin-7-yl}-3-[4-(methylthio)phenyl]urea | Interm. 18 (methylthio)phenyl isocyanate | ¹H NMR (300 MHz, CD₃OD) δ: 2.42 (s, 3 H), 2.82-2.96 (m, 1 H), 2.97-3.10 (m, 1 H), 3.10-3.24 (m, 2 H), 3.32-3.45 (m, 1 H), 4.33-4.48 (m, 1 H), 4.76 (d, J = 5.3 Hz, 1 H), 6.89 (s, 1 H), 6.95 (d, J = 7.9 Hz, 1 H), 7.08 (dd, J = 8.6, 4.2 Hz, 1 H), 7.22 (d, J = 8.8 Hz, 2 H), 7.31-7.45 (m, 3 H), 7.53 (dd, J = 8.1, 2.2 Hz, 1 H), 7.61 (s, 1 H), 7.94 (d, J = 1.8 Hz, 1 H), 8.32 (d, J = 2.6 Hz, 1H) | yellow solid |

TABLE 7-continued

| Comp. No. | IUPAC name | Reactants | ¹H NMR δ (ppm) for Compound | Features |
|---|---|---|---|---|
| 23 | 1-{3-(2-furyl)-2-[2-(1H-imidazol-4-yl)ethyl]-1-oxo-1,2,3,4-tetrahydroisoquinolin-7-yl}-3-[4-(methylthio)phenyl]urea | Interm. 19 4-(methylthio)-phenyl isocyanate | ¹H NMR (300 MHz, CD$_3$OD) δ: 2.41 (s, 3 H), 2.81-3.12 (m, 3 H), 3.17-3.29 (m, 1 H), 3.33-3.40 (m, 1 H), 4.31 (ddd, J = 13.3, 7.7, 5.4 Hz, 1 H), 4.71 (d, J = 4.7 Hz, 1 H), 5.93 (d, J = 2.9 Hz, 1 H), 6.19 (br.s., 1 H), 6.87 (s, 1 H), 7.08 (d, J = 8.2 Hz, 1 H), 7.21 (d, J = 8.5 Hz, 2 H), 7.31 (s, 1 H), 7.35 (s, 1 H), 7.37 (s, 1 H), 7.59 (d, J = 2.3 Hz, 1 H), 7.63 (s, 1 H), 7.90 (d, J = 2.1 Hz, 1 H). | yellow solid |
| 24 | 1-{3-(5-chloro-2-furyl)-2-[2-(1H-imidazol-4-yl)ethyl]-1-oxo-1,2,3,4-tetrahydroisoquinolin-7-yl}-3-[4-(methylthio)phenyl]urea | Interm. 32 4-(methylthio)-phenyl isocyanate | ¹H NMR (300 MHz, CD$_3$OD) δ: 2.42 (s, 3 H), 2.81-3.10 (m, 3 H), 3.16-3.28 (m, 1 H), 3.32-3.39 (m, 1 H), 4.25-4.41 (m, 1 H), 4.68 (d, J = 4.4 Hz, 1 H), 5.96 (d, J = 3.2 Hz, 1 H), 6.04 (d, J = 3.2 Hz, 1 H), 6.89 (s, 1 H), 7.11 (d, J = 8.2 Hz, 1 H), 7.22 (d, J = 8.5 Hz, 2 H), 7.29-7.43 (m, 3 H), 7.57-7.67 (m, 2 H), 7.91 (d, J = 1.8 Hz, 1 H). | yellow solid |
| 25 | 1-(4-acetylphenyl)-3-{3-(6-chloropyridin-3-yl)-2-[2-(1H-imidazol-4-yl)ethyl]-1-oxo-1,2,3,4-tetrahydroisoquinolin-7-yl}urea | Interm. 33 4-acetylphenyl isocyanate | ¹H NMR (300 MHz, CD$_3$OD) δ: 2.56 (s, 3 H), 2.87-3.09 (m, 3 H), 3.17-3.28 (m, 1 H), 3.47 (dd, J = 16.0, 6.6 Hz, 1 H), 4.25-4.35 (m, 1 H), 4.87 (br.s., 1 H), 6.90 (s, 1 H), 7.04 (d, J = 8.2 Hz, 1 H), 7.29 (d, J = 8.2 Hz, 1 H), 7.45 (dd, J = 8.4, 2.5 Hz, 1 H), 7.56-7.64 (m, 4 H), 7.94 (s, 1 H), 7.97 (s, 1 H), 8.02 (d, J = 2.1 Hz, 1 H), 8.09 (d, J = 2.3 Hz, 1 H) | white solid |

TABLE 7-continued

| Comp. No. | IUPAC name | Reactants | $^1$H NMR δ (ppm) for Compound | Features |
|---|---|---|---|---|
| 26 | 1-{3-(6-chloropyridin-3-yl)-2-[2-(1H-imidazol-4-yl)ethyl]-1-oxo-1,2,3,4-tetrahydroisoquinolin-7-yl}-3-[4-(methylthio)phenyl]urea | Interm. 33 4-(methylthio)-phenyl isocyanate | $^1$H NMR (300 MHz, CD$_3$OD) δ: 2.44 (s, 3 H), 2.85-3.09 (m, 3 H), 3.16-3.28 (m, 1 H), 3.46 (dd, J = 15.5, 6.4 Hz, 1 H), 4.24-4.35 (m, 1 H), 4.87 (br.s., 1 H), 6.89 (s, 1 H), 7.01 (d, J = 8.2 Hz, 1 H), 7.21-7.32 (m, 3 H), 7.38 (d, J = 8.8 Hz, 2 H), 7.44 (dd, J = 8.2, 2.3 Hz, 1 H), 7.58 (d, J = 2.3 Hz, 1 H), 7.61 (s, 1 H), 7.98 (d, J = 2.1 Hz, 1 H), 8.09 (d, J = 2.1 Hz, 1 H) | white solid |
| 27 | 1-(4-acetylphenyl)-3-{3-(5-chloropyridin-2-yl)-2-[2-(1H-imidazol-4-yl)ethyl]-1-oxo-1,2,3,4-tetrahydroquinolin-7-yl}urea | Interm. 34 4-acetylphenyl isocyanate | $^1$H NMR (300 MHz, CD$_3$OD) δ: 8.40 (s, 1H), 7.89-8.00 (m, 3H), 7.60-7.68 (m, 2H), 7.50-7.60 (m, 3H), 7.05 (d, J = 7.9 Hz, 1H), 6.97 (d, J = 8.2 Hz, 1H), 6.89 (s, 1H), 4.76 (d, J = 5.9 Hz, 1H), 4.33-4.48 (m, 1H), 3.33-3.45 (m, 1H), 3.12-3.26 (m, 2H), 2.96-3.12 (m, 1H), 2.83-2.96 (m, 1H), 2.54 (s, 3H) | yellow solid |
| 28 | 1-{3-(5-chloropyridin-2-yl)-2-[2-(1H-imidazol-4-yl)ethyl]-1-oxo-1,2,3,4-tetrahydro isoquinolin-7-yl}-3-[4-(methylthio)phenyl]urea | Interm. 34 4-(methylthio)-phenyl isocyanate | $^1$H NMR (300 MHz, CD$_3$OD) δ: 8.39 (s, 1H), 7.95 (s, 1H), 7.56-7.66 (m, 2H), 7.51 (d, J = 8.2 Hz, 1H), 7.29-7.42 (m, 2H), 7.20 (d, J = 7.9 Hz, 2H), 7.03 (d, J = 8.5 Hz, 1H), 6.94 (d, J = 8.2 Hz, 1H), 6.88 (s, 1H), 4.75 (d, J = 6.2 Hz, 1H), 4.31-4.48 (m, 1H), 3.33-3.45 (m, 1H), 3.10-3.27 (m, 2H), 2.97-3.10 (m, 1H), 2.82-2.95 (m, 1H), 2.41 (s, 3H) | yellow solid |

Compounds 29, 30, 31 and 32 were synthesized by using 5.0 equivalents of meta-chloroperbenzoic acid in the procedure of Example 5 for Intermediate 35 and stirring the reaction mixture at 25° C. for 0.5 h lead to the sulfonyl derivatives. The sterting materials used and the results are described below in Table 8.

TABLE 8

| Comp No. | IUPAC name | Starting material | $^1$H NMR δ (ppm) for Compound | Features |
|---|---|---|---|---|
| 29 | 1-{3-(4-cyanophenyl)-2-[2-(1H-imidazol-4-yl)ethyl]-1-oxo-1,2,3,4-tetrahydroisoquinolin-7-yl}-3-[4-(methylsulfinyl)phenyl]urea | Interm. 15 | $^1$H NMR (300 MHz, CD$_3$OD) δ: 2.43 (s, 3 H), 2.82-3.21 (m, 4 H), 3.45 (dd, J = 16.0, 6.6 Hz, 1 H), 4.27-4.39 (m, 1 H), 4.86-4.90 (m, 1 H), 6.89 (s, 1 H), 6.96 (d, J = 8.5 Hz, 1 H), 7.20-7.27 (m, 4 H), 7.36 (s, 1 H), 7.39 (s, 1 H), 7.50-7.64 (m, 4 H), 7.97 (d, J = 2.1 Hz, 1 H). | white solid |
| 30 | 1-{3-(4-cyanophenyl)-2-[2-(1H-imidazol-4-yl)ethyl]-1-oxo-1,2,3,4-tetrahydroisoquinolin-7-yl}-3-[4-(methylsulfonyl)phenyl]urea | Comp. 21 | $^1$H NMR (CD$_3$OD) δ: 2.84-3.07 (m, 4 H), 3.09 (s, 3 H), 3.10-3.22 (m, 1 H), 3.47 (dd, J = 16.0, 6.6 Hz, 1 H), 4.34 (ddd, J = 13.1, 7.7, 5.6 Hz, 1 H), 6.90 (s, 1 H), 6.99 (d, J = 8.2 Hz, 1 H), 7.24 (d, J = 8.2 Hz, 2 H), 7.52-7.58 (m, 2 H), 7.61 (d, J = 7.6 Hz, 2 H), 7.68 (s, 1 H), 7.71 (s, 1 H), 7.83 (s, 1 H), 7.86 (s, 1 H), 8.04 (d, J = 2.3 Hz, 1 H). | white solid |
| 31 | 1-{3-(5-fluoropyridin-2-yl)-2-[2-(1H-imidazol-4-yl)ethyl]-1-oxo-1,2,3,4-tetrahydro isoquinolin-7-yl}-3-[4-(methylsulfinyl)phenyl]urea | Comp. 22 | $^1$H NMR (300 MHz, CD$_3$OD) δ: 2.78 (s, 3 H), 2.84-2.96 (m, 1 H), 2.98-3.11 (m, 1 H), 3.11-3.25 (m, 2 H), 3.33-3.45 (m, 1 H), 4.35-4.48 (m, 1 H), 4.78 (d, J = 6.4 Hz, 1 H), 6.90 (s, 1 H), 6.98 (d, J = 8.5 Hz, 1 H), 7.10 (dd, J = 9.2, 3.7 Hz, 1 H), 7.42 (t, J = 9.2 Hz, 1 H), 7.55 (d, J = 8.5 Hz, 1 H), 7.60-7.73 (m, 5 H), 7.97 (s, 1 H), 8.33 (s, 1 H). | white solid |

TABLE 8-continued

| Comp No. | IUPAC name | Starting material | $^1$H NMR δ (ppm) for Compound | Features |
|---|---|---|---|---|
| 32 | 1-{3-(5-fluoropyridin-2-yl)-2-[2-(1H-imidazol-4-yl)ethyl]-1-oxo-1,2,3,4-tetrahydro isoquinolin-7-yl}-3-[4-(methylsulfonyl)phenyl]urea | Comp. 22 | $^1$H NMR (CD$_3$OD) δ: 2.84-2.97 (m, 1 H), 2.97-3.05 (m, 1 H), 3.08 (s, 3 H), 3.11-3.25 (m, 2 H), 3.32-3.44 (m, 1 H), 4.40 (dt, J = 13.5, 6.7 Hz, 1 H), 4.78 (d, J = 5.9 Hz, 1 H), 6.89 (s, 1 H), 6.97 (d, J = 7.9 Hz, 1 H), 7.09 (dd, J = 8.4, 3.7 Hz, 1 H), 7.40 (t, J = 8.5 Hz, 1 H), 7.53 (d, J = 8.2 Hz, 1 H), 7.62 (s, 1 H), 7.69 (d, J = 1.5 Hz, 2 H), 7.78-7.86 (m, 2 H), 7.99 (s, 1 H), 8.31 (s, 1 H). | white solid |
| 34 | 1-{3-(5-chloropyridin-2-yl)-2-[2-(1H-imidazol-4-yl)ethyl]-1-oxo-1,2,3,4-tetrahydro isoquinolin-7-yl}-3-[4-(methylsulfonyl)phenyl]urea | Comp. 28 | $^1$H NMR (CD$_3$OD) δ: 8.41 (d, J = 1.2 Hz, 1H), 7.98 (s, 1H), 7.84 (d, J = 8.8 Hz, 2H), 7.60-7.74 (m, 4H), 7.55 (d, J = 6.7 Hz, 1H), 7.06 (d, J = 8.5 Hz, 1H), 6.99 (d, J = 7.9 Hz, 1H), 6.89 (s, 1H), 4.77 (d, J = 5.9 Hz, 1H), 4.34-4.48 (m, 1H), 3.33-3.45 (m, 1H), 3.13-3.26 (m, 2H), 3.08 (s, 3H), 2.97-3.06 (m, 1H), 2.83-2.98 (m, 1H). | light yellow solid |

Example 8

Biological Data

Biological activity of compounds according to Formula 1 is set forth in Table 9 below. CHO—Gα16 cells stably expressing FPRL1 were cultured in (F12, 10% FBS, 1% PSA, 400 μg/ml geneticin and 50 μg/ml hygromycin) and HEK-Gqi5 cells stable expressing FPR1 were cultured in (DMEM high glucose, 10% FBS, 1% PSA, 400 μg/ml geneticin and 50 μg/ml hygromycin). In general, the day before the experiment, 18,000 cells/well were plated in a 384-well clear bottom poly-d-lysine coated plate. The following day the screening compound-induced calcium activity was assayed on the FLIPR$^{Tetra}$. The drug plates were prepared in 384-well microplates using the EP3 and the MultiPROBE robotic liquid handling systems. Compounds were tested at concentrations ranging from 0.61 to 10,000 nM. Results are expressed as EC$_{50}$ (nM) and efficacy values.

TABLE 9

| IUPAC name | FPRL-1 Gα16-CHO EC$_{50}$ (eff) |
|---|---|
| 1-(4-acetylphenyl)-3-[2-(3-aminopropyl)-3-(4-cyanophenyl)-1-oxo-1,2,3,4-tetrahydroisoquinolin-7-yl]urea | 40 nM (1.00) |
| 1-(4-acetylphenyl)-3-[2-(2-aminoethyl)-3-(4-cyanophenyl)-1-oxo-1,2,3,4-tetrahydroisoquinolin-7-yl]urea | 34 nM (0.90) |
| 1-(4-acetylphenyl)-3-{3-(4-cyanophenyl)-2-[2-(1H-imidazol-4-yl)ethyl]-1-oxo-1,2,3,4-tetrahydroisoquinolin-7-yl}urea | 11 nM (0.80) |
| 1-(4-acetylphenyl)-3-{3-(4-cyanophenyl)-2-[2-(methylamino)ethyl]-1-oxo-1,2,3,4-tetrahydroisoquinolin-7-yl}urea | 32 nM (1.00) |
| 1-[2-(3-aminopropyl)-3-(4-cyanophenyl)-1-oxo-1,2,3,4-tetrahydroisoquinolin-7-yl]-3-[4-(trifluoromethyl)phenyl]urea | 21 nM (0.78) |

TABLE 9-continued

| IUPAC name | FPRL-1 Ga16-CHO EC$_{50}$ (eff) |
|---|---|
| 1-{3-(4-cyanophenyl)-2-[2-(1H-imidazol-4-yl)ethyl]-1-oxo-1,2,3,4-tetrahydroisoquinolin-7-yl}-3-[4-(trifluoromethyl)phenyl]urea | 32 nM (0.78) |
| 1-[2-(3-aminopropyl)-3-(4-cyanophenyl)-1-oxo-1,2,3,4-tetrahydroisoquinolin-7-yl]-3-[4-(methylthio)phenyl]urea | 2.5 nM (0.70) |
| 1-(4-acetylphenyl)-3-{3-(3,4-dichlorophenyl)-2-[2-(1H-imidazol-4-yl)ethyl]-1-oxo-1,2,3,4-tetrahydroisoquinolin-7-yl}urea | 28 nM (1.04) |
| 1-[2-(3-aminopropyl)-3-(4-cyanophenyl)-1-oxo-1,2,3,4-tetrahydroisoquinolin-7-yl]-3-(4-bromophenyl)urea. | 31 nM (1.00) |
| 1-[2-(3-aminopropyl)-3-(4-cyanophenyl)-1-oxo-1,2,3,4-tetrahydroisoquinolin-7-yl]-3-[4-(methylsulfinyl)phenyl]urea | 21 nM (0.92) |
| 1-[2-(3-aminopropyl)-3-(4-cyanophenyl)-1-oxo-1,2,3,4-tetrahydroisoquinolin-7-yl]-3-[4-(methylsulfonyl)phenyl]urea | 10 nM (0.86) |
| 1-{3-(4-cyanophenyl)-2-[2-(1H-imidazol-4-yl)ethyl]-1-oxo-1,2,3,4-tetrahydroisoquinolin-7-yl}-3-[4-(methylsulfinyl)phenyl]urea | 22 nM (0.96) |
| 1-{3-(4-cyanophenyl)-2-[2-(1H-imidazol-4-yl)ethyl]-1-oxo-1,2,3,4-tetrahydroisoquinolin-7-yl}-3-[4-(methylsulfonyl)phenyl]urea | 20 nM (1.00) |
| 1-{3-(6-fluoropyridin-3-yl)-2-[2-(1H-imidazol-4-yl)ethyl]-1-oxo-1,2,3,4-tetrahydroisoquinolin-7-yl}-3-[4-(methylthio)phenyl]urea | 12.6 nM (0.93) |
| 1-{3-(2-furyl)-2-[2-(1H-imidazol-4-yl)ethyl]-1-oxo-1,2,3,4-tetrahydroisoquinolin-7-yl}-3-[4-(methylthio)phenyl]urea | 19 nM (0.83) |
| 1-{3-(5-fluoropyridin-2-yl)-2-[2-(1H-imidazol-4-yl)ethyl]-1-oxo-1,2,3,4-tetrahydroisoquinolin-7-yl}-3-[4-(methylsulfinyl)phenyl]urea | 11.8 nM (0.93) |
| 1-{3-(5-fluoropyridin-2-yl)-2-[2-(1H-imidazol-4-yl)ethyl]-1-oxo-1,2,3,4-tetrahydro isoquinolin-7-yl}-3-[4-(methylsulfonyl)phenyl]urea | 10.5 nM (1.0) |
| 1-{3-(5-chloro-2-furyl)-2-[2-(1H-imidazol-4-yl)ethyl]-1-oxo-1,2,3,4-tetrahydroisoquinolin-7-yl}-3-[4-(methylthio)phenyl]urea | 17 nM (0.81) |
| 1-(4-acetylphenyl)-3-{3-(6-chloropyridin-3-yl)-2-[2-(1H-imidazol-4-yl)ethyl]-1-oxo-1,2,3,4-tetrahydroisoquinolin-7-yl}urea | 24 nM (0.81) |
| 1-{3-(6-chloropyridin-3-yl)-2-[2-(1H-imidazol-4-yl)ethyl]-1-oxo-1,2,3,4-tetrahydroisoquinolin-7-yl}-3-[4-(methylthio)phenyl]urea | 6.3 nM (0.89) |
| 1-(4-acetylphenyl)-3-{3-(5-chloropyridin-2-yl)-2-[2-(1H-imidazol-4-yl)ethyl]-1-oxo-1,2,3,4-tetrahydroisoquinolin-7-yl}urea | 38.4 nM (81) |
| 1-{3-(5-chloropyridin-2-yl)-2-[2-(1H-imidazol-4-yl)ethyl]-1-oxo-1,2,3,4-tetrahydro isoquinolin-7-yl}-3-[4-(methylthio)phenyl]urea | 13.5 nM (0.91) |
| 1-{3-(5-chloropyridin-2-yl)-2-[2-(1H-imidazol-4-yl)ethyl]-1-oxo-1,2,3,4-tetrahydro isoquinolin-7-yl}-3-[4-(methylsulfonyl)phenyl]urea | 9.5 nM (0.99) |
| 1-[2-(3-aminopropyl)-3-(4-cyanophenyl)-1-oxo-1,2,3,4-tetrahydroisoquinolin-7-yl]-3-[4-(ethylthio)phenyl]urea | 23 nM (1.0) |
| (S)-[2-(3-aminopropyl)-3-(4-cyanophenyl)-1-oxo-1,2,3,4-tetrahydroisoquinolin-7-yl]-3-[4-(methylthio)phenyl]urea. | 299 nM (1.0) |
| (R)-1-[2-(3-aminopropyl)-3-(4-cyanophenyl)-1-oxo-1,2,3,4-tetrahydroisoquinolin-7-yl]-3-[4-(methylthio)phenyl]urea. | 3.3 nM (0.97) |
| (S)-1-[2-(3-aminopropyl)-3-(4-cyanophenyl)-1-oxo-1,2,3,4-tetrahydroisoquinolin-7-yl]-3-[4-(methylsulfinyl)phenyl]urea | 878 nM (0.85) |
| (S)-1-[2-(3-aminopropyl)-3-(4-cyanophenyl)-1-oxo-1,2,3,4-tetrahydroisoquinolin-7-yl]-3-[4-(methylsulfinyl)phenyl]urea | 10.6 nM (0.94) |
| (S)-1-[2-(3-aminopropyl)-3-(4-cyanophenyl)-1-oxo-1,2,3,4-tetrahydroisoquinolin-7-yl]-3-[4-(methylsulfonyl)phenyl]urea | ND (1.3) |
| (R)-1-[2-(3-aminopropyl)-3-(4-cyanophenyl)-1-oxo-1,2,3,4-tetrahydroisoquinolin-7-yl]-3-[4-(methylsulfonyl)phenyl]urea | 29 nM (0.90) |
| 1-[2-(3-aminopropyl)-3-methyl-1-oxo-1,2,3,4-tetrahydroisoquinolin-7-yl]-3-[4-(methylthio)phenyl]urea | 15 nM (0.89) |
| 1-[2-(3-aminopropyl)-3-methyl-1-oxo-1,2,3,4-tetrahydroisoquinolin-7-yl]-3-[4-(methylsulfonyl)phenyl]urea | 150 nM (88) |

What is claimed is:

1. A compound having Formula I, its enantiomers, diastereoisomers, crystal forms and individual isomers, tautomers or a pharmaceutically acceptable salt thereof,

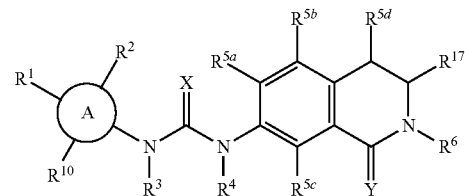

Formula I wherein:

A is $C_{6-10}$ aryl, Heterocyle, $C_{3-8}$ cycloalkyl or $C_{3-8}$ cycloalkenyl;

$R^{17}$ is $C_{1-6}$ alkyl or

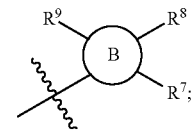

B is $C_{6-10}$ aryl, Heterocyle, $C_{3-8}$ cycloalkyl or $C_{3-8}$ cycloalkenyl;

$R^1$ is H, halogen, —S(O)$R^{15}$, —S(O)$_2R^{11}$, nitro, cyano, —OC$_{1-6}$ alkyl, —SC$_{1-6}$ alkyl, —C$_{1-6}$ alkyl, —C$_{2-6}$ alkenyl, —C$_{2-6}$ alkynyl, C(O)$R^{12}$, NR$^{13}R^{14}$, $C_{3-8}$ cycloalkyl or hydroxyl;

$R^2$ is H, halogen, —S(O)$R^{15}$, —S(O)$_2R^{11}$, nitro, cyano, —OC$_{1-6}$ alkyl, —SC$_{1-6}$ alkyl, —C$_{1-6}$ alkyl, —C$_{2-6}$ alkenyl, —C$_{2-6}$ alkynyl, C(O)$R^{12}$, NR$^{13}R^{14}$, $C_{3-8}$ cycloalkyl or hydroxyl;

$R^3$ is H, $C_{1-6}$ alkyl or $C_{3-8}$ cycloalkyl;

$R^4$ is H, $C_{1-6}$ alkyl or $C_{3-8}$ cycloalkyl;

$R^{5a}$ is H, halogen, —S(O)$R^{15}$, —S(O)$_2R^{11}$, nitro, cyano, —OC$_{1-6}$ alkyl, —SC$_{1-6}$ alkyl, —C$_{1-6}$ alkyl, —C$_{2-6}$ alkenyl, —C$_{2-6}$ alkynyl, C(O)$R^{12}$, NR$^{13}R^{14}$, $C_{3-8}$ cycloalkyl or hydroxyl;

$R^{5b}$ is H, halogen, —S(O)$R^{15}$, —S(O)$_2R^{11}$, nitro, cyano, —OC$_{1-6}$ alkyl, —SC$_{1-6}$ alkyl, —C$_{1-6}$ alkyl, —C$_{2-6}$ alkenyl, —C$_{2-6}$ alkynyl, C(O)$R^{12}$, NR$^{13}R^{14}$, $C_{3-8}$ cycloalkyl or hydroxyl;

$R^{5c}$ is H, halogen, —S(O)$R^{15}$, —S(O)$_2R^{11}$, nitro, cyano, —OC$_{1-6}$ alkyl, —SC$_{1-6}$ alkyl, —C$_{1-6}$ alkyl, —C$_{2-6}$ alkenyl, —C$_{2-6}$ alkynyl, C(O)$R^{12}$, NR$^{13}R^{14}$, $C_{3-8}$ cycloalkyl or hydroxyl;

$R^{5d}$ is H, halogen, —S(O)$R^{15}$, —S(O)$_2R^{11}$, nitro, cyano, —O$C_{1-6}$ alkyl, —S$C_{1-6}$ alkyl, —$C_{1-6}$ alkyl, —$C_{2-6}$ alkenyl, —$C_{2-6}$ alkynyl, C(O)$R^{12}$, $NR^{13}R^{14}$, $C_{3-8}$ cycloalkyl or hydroxyl;

$R^6$ is H, —S(O)$_2R^{11}$, —$C_{1-6}$ alkyl, C(O)$R^{12}$, —(CH$_2$)$_n$$NR^{13}R^{14}$, —(CH$_2$)$_m$ heterocycle, $NR^{13}R^{14}$, $C_{3-8}$ cycloalkyl, $C_{6-10}$ aryl, or heterocycle;

$R^7$ is H, halogen, —S(O)$R^{15}$, —S(O)$_2R^{11}$, nitro, cyano, —O$C_{1-6}$ alkyl, —S$C_{1-6}$ alkyl, —$C_{1-6}$ alkyl, —$C_{2-6}$ alkenyl, —$C_{2-6}$ alkynyl, C(O)$R^{12}$, $NR^{13}R^{14}$, $C_{3-8}$ cycloalkyl or hydroxyl;

$R^8$ is H, halogen, —S(O)$R^{15}$, —S(O)$_2R^{11}$, nitro, cyano, —O$C_{1-6}$ alkyl, —S$C_{1-6}$ alkyl, —$C_{1-6}$ alkyl, —$C_{2-6}$ alkenyl, —$C_{2-6}$ alkynyl, C(O)$R^{12}$, $NR^{13}R^{14}$, $C_{3-8}$ cycloalkyl or hydroxyl;

$R^9$ is H, halogen, —S(O)$R^{15}$, —S(O)$_2R^{11}$, nitro, cyano, —O$C_{1-6}$ alkyl, —S$C_{1-6}$ alkyl, —$C_{1-6}$ alkyl, —$C_{2-6}$ alkenyl, —$C_{2-6}$ alkynyl, C(O)$R^{12}$, $NR^{13}R^{14}$, $C_{3-8}$ cycloalkyl or hydroxyl;

$R^{10}$ is H, halogen, —S(O)$R^{15}$, —S(O)$_2R^{11}$, nitro, cyano, —O$C_{1-6}$ alkyl, —S$C_{1-6}$ alkyl, —$C_{1-6}$ alkyl, —$C_{2-6}$ alkenyl, —$C_{2-6}$ alkynyl, C(O)$R^{12}$, $NR^{13}R^{14}$, $C_{3-8}$ cycloalkyl or hydroxyl;

X is O or S;

Y is O or S;

$R^{11}$ is H, hydroxyl, —$C_{1-6}$ alkyl, $C_{3-8}$ cycloalkyl or $NR^{13}R^{14}$;

$R^{12}$ is H, hydroxyl, —$C_{1-6}$ alkyl, hydroxyl, $C_{3-8}$ cycloalkyl, $NR^{13}R^{14}$ or —O$C_{1-6}$ alkyl;

$R^{13}$ is H, —$C_{1-6}$ alkyl, $C_{3-8}$ cycloalkyl, SO$_2R^{11}$ or C(O)$R^{16}$;

$R^{14}$ is H, —$C_{1-6}$ alkyl or $C_{3-8}$ cycloalkyl;

$R^{15}$ is —$C_{1-6}$ alkyl, or $C_{3-8}$ cycloalkyl;

$R^{16}$ is H, —$C_{1-6}$ alkyl or $C_{3-8}$ cycloalkyl;

n is 1-4; and m is 1-4.

2. A compound according to claim 1, wherein:

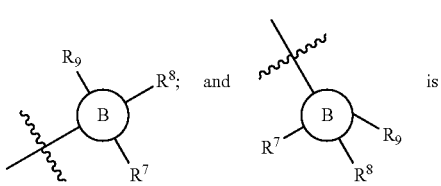

,

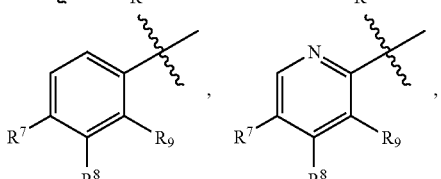

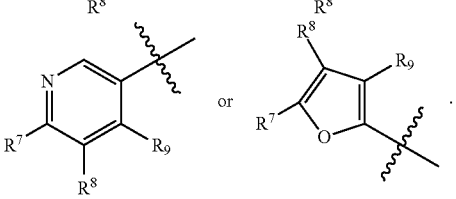

3. A compound according to claim 1, wherein:

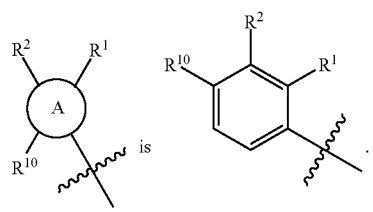

4. A compound according to claim 1, wherein:

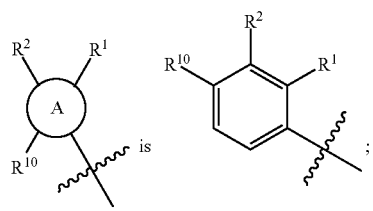

$R^{17}$ is

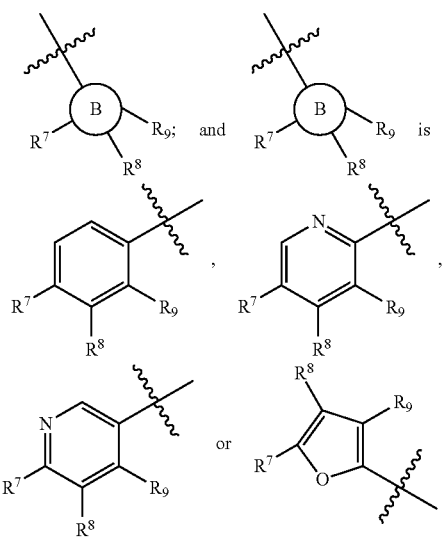

5. A compound according to claim 1, wherein:

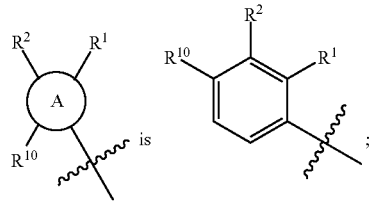

$R^{17}$ is $C_{1-6}$ alkyl;
$R^1$ is H;
$R^2$ is H;
$R^3$ is H;
$R^4$ is H;

$R^{5a}$ is H;
$R^{5b}$ is H;
$R^{5c}$ is H;
$R^{5d}$ is H;
$R^6$ is H, —(CH$_2$)$_n$ NR$^{13}$R$^{14}$, —(CH$_2$)$_m$ heterocycle or —C$_{1-6}$ alkyl;
$R^{10}$ is halogen, —S(O)R$^{15}$, —S(O)$_2$R$^{11}$, —SC$_{1-6}$ alkyl, —C$_{1-6}$ alkyl or C(O)R$^{12}$;
X is O;
Y is O;
$R^{11}$ is —C$_{1-6}$ alkyl;
$R^{12}$ is —C$_{1-6}$ alkyl;
$R^{13}$ is H or —C$_{1-6}$ alkyl;
$R^{14}$ is H or —C$_{1-6}$ alkyl;
$R^{15}$ is —C$_{1-6}$ alkyl; and
n is 1-4; and
m is 1-4.

6. A compound according to claim 1, wherein:

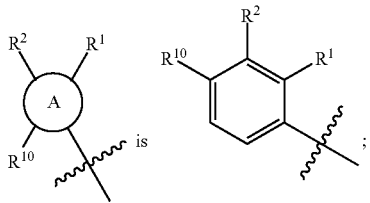

$R^{17}$ is

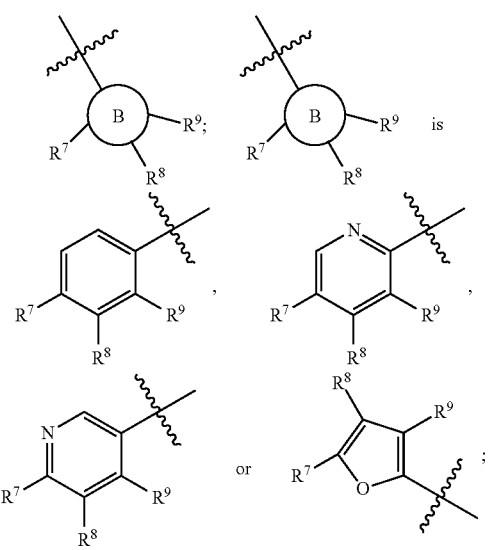

$R^1$ is H;
$R^2$ is H;
$R^3$ is H;
$R^4$ is H;
$R^{5a}$ is H;
$R^{5b}$ is H;
$R^{5c}$ is H;
$R^{5d}$ is H;
$R^6$ is H, —(CH$_2$)$_n$ NR$^{13}$R$^{14}$, —(CH$_2$)$_m$ heterocycle or —C$_{1-6}$ alkyl;
$R^7$ is H, halogen or cyano;
$R^8$ is H or halogen;
$R^9$ is H;
$R^{10}$ is halogen, —S(O)R$^{15}$, —S(O)$_2$R$^{11}$, —SC$_{1-6}$ alkyl, —C$_{1-6}$ alkyl or C(O)R$^{12}$;
X is O;
Y is O;
$R^{11}$ is —C$_{1-6}$ alkyl;
$R^{12}$ is —C$_{1-6}$ alkyl;
$R^{13}$ is H or —C$_{1-6}$ alkyl;
$R^{14}$ is H or —C$_{1-6}$ alkyl;
$R^{15}$ is —C$_{1-6}$ alkyl;
n is 1-4; and
m is 1-4.

7. A compound according to claim 6, wherein:

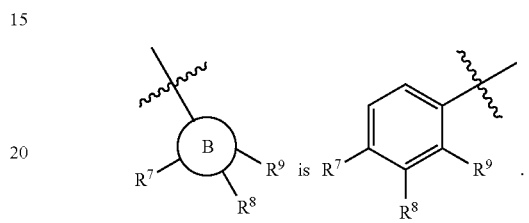

8. A compound according to claim 6, wherein:

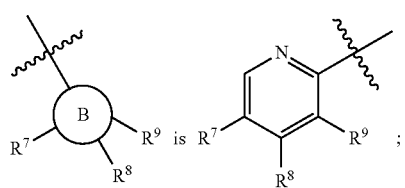

$R^7$ is halogen;
$R^8$ is H; and
$R^{10}$ is —S(O)R$^{15}$, —S(O)$_2$R$^{11}$, —SC$_{1-6}$ alkyl, or C(O)R$^{12}$.

9. A compound according to claim 6, wherein:

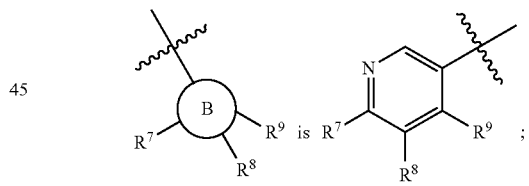

$R^7$ is halogen;
$R^8$ is H; and
$R^{10}$ is —SC$_{1-6}$alkyl or C(O)R$^{12}$.

10. A compound according to claim 6, wherein:

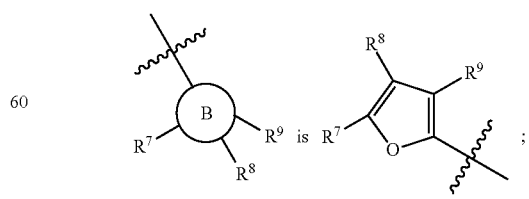

$R^7$ is H or halogen; and
$R^{10}$ is —SC$_{1-6}$alkyl.

11. A compound according to claim 1 selected from:
1-(4-acetylphenyl)-3-[2-(3-aminopropyl)-3-(4-cyanophenyl)-1-oxo-1,2,3,4-tetrahydroisoquinolin-7-yl]urea;
1-(4-acetylphenyl)-3-[2-(2-aminoethyl)-3-(4-cyanophenyl)-1-oxo-1,2,3,4-tetrahydroisoquinolin-7-yl]urea;
1-(4-acetylphenyl)-3-{3-(4-cyanophenyl)-2-[2-(1H-imidazol-4-yl)ethyl]-1-oxo-1,2,3,4-tetrahydroisoquinolin-7-yl}urea;
1-(4-acetylphenyl)-3-{3-(4-cyanophenyl)-2-[2-(methylamino)ethyl]-1-oxo-1,2,3,4-tetrahydroisoquinolin-7-yl}urea;
1-[2-(3-aminopropyl)-3-(4-cyanophenyl)-1-oxo-1,2,3,4-tetrahydroisoquinolin-7-yl]-3-[4-(trifluoromethyl)phenyl]urea;
1-{3-(4-cyanophenyl)-2-[2-(1H-imidazol-4-yl)ethyl]-1-oxo-1,2,3,4-tetrahydroisoquinolin-7-yl}-3-[4-(trifluoromethyl)phenyl]urea;
1-[2-(3-aminopropyl)-3-(4-cyanophenyl)-1-oxo-1,2,3,4-tetrahydroisoquinolin-7-yl]-3-[4-(methylthio)phenyl]urea;
1-(4-acetylphenyl)-3-{3-(3,4-dichlorophenyl)-2-[2-(1H-imidazol-4-yl)ethyl]-1-oxo-1,2,3,4-tetrahydroisoquinolin-7-yl}urea;
1-[2-(3-aminopropyl)-3-(4-cyanophenyl)-1-oxo-1,2,3,4-tetrahydroisoquinolin-7-yl]-3-(4-bromophenyl)urea;
1-[2-(3-aminopropyl)-3-(4-cyanophenyl)-1-oxo-1,2,3,4-tetrahydroisoquinolin-7-yl]-3-[4-(methylsulfinyl)phenyl]urea;
1-[2-(3-aminopropyl)-3-(4-cyanophenyl)-1-oxo-1,2,3,4-tetrahydroisoquinolin-7-yl]-3-[4-(methylsulfonyl)phenyl]urea;
1-{3-(4-cyanophenyl)-2-[2-(1H-imidazol-4-yl)ethyl]-1-oxo-1,2,3,4-tetrahydroisoquinolin-7-yl}-3-[4-(methylthio)phenyl]urea;
1-{3-(4-cyanophenyl)-2-[2-(1H-imidazol-4-yl)ethyl]-1-oxo-1,2,3,4-tetrahydroisoquinolin-7-yl}-3-[4-(methylsulfinyl)phenyl]urea;
1-{3-(4-cyanophenyl)-2-[2-(1H-imidazol-4-yl)ethyl]-1-oxo-1,2,3,4-tetrahydroisoquinolin-7-yl}-3-[4-(methylsulfonyl)phenyl]urea;
1-{3-(6-fluoropyridin-3-yl)-2-[2-(1H-imidazol-4-yl)ethyl]-1-oxo-1,2,3,4-tetrahydroisoquinolin-7-yl}-3-[4-(methylthio)phenyl]urea;
1-{3-(5-fluoropyridin-2-yl)-2-[2-(1H-imidazol-4-yl)ethyl]-1-oxo-1,2,3,4-tetrahydro isoquinolin-7-yl}-3-[4-(methylsulfinyl)phenyl]urea;
1-{3-(5-fluoropyridin-2-yl)-2-[2-(1H-imidazol-4-yl)ethyl]-1-oxo-1,2,3,4-tetrahydro isoquinolin-7-yl}-3-[4-(methylsulfonyl)phenyl]urea;
1-{3-(2-furyl)-2-[2-(1H-imidazol-4-yl)ethyl]-1-oxo-1,2,3,4-tetrahydroisoquinolin-7-yl}-3-[4-(methylthio)phenyl]urea;
1-{3-(5-chloro-2-furyl)-2-[2-(1H-imidazol-4-yl)ethyl]-1-oxo-1,2,3,4-tetrahydroisoquinolin-7-yl}-3-[4-(methylthio)phenyl]urea;
1-(4-acetylphenyl)-3-{3-(6-chloropyridin-3-yl)-2-[2-(1H-imidazol-4-yl)ethyl]-1-oxo-1,2,3,4-tetrahydroisoquinolin-7-yl}urea;
1-{3-(6-chloropyridin-3-yl)-2-[2-(1H-imidazol-4-yl)ethyl]-1-oxo-1,2,3,4-tetrahydroisoquinolin-7-yl}-3-[4-(methylthio)phenyl]urea;
1-(4-acetylphenyl)-3-{3-(5-chloropyridin-2-yl)-2-[2-(1H-imidazol-4-yl)ethyl]-1-oxo-1,2,3,4-tetrahydroisoquinolin-7-yl}urea;
1-{3-(5-chloropyridin-2-yl)-2-[2-(1H-imidazol-4-yl)ethyl]-1-oxo-1,2,3,4-tetrahydro isoquinolin-7-yl}-3-[4-(methylthio)phenyl]urea;
1-{3-(5-chloropyridin-2-yl)-2-[2-(1H-imidazol-4-yl)ethyl]-1-oxo-1,2,3,4-tetrahydro isoquinolin-7-yl}-3-[4-(methylsulfonyl)phenyl]urea;
1-[2-(3-aminopropyl)-3-(4-cyanophenyl)-1-oxo-1,2,3,4-tetrahydroisoquinolin-7-yl]-3-[4-(ethylthio)phenyl]urea;
(S)-1-[2-(3-aminopropyl)-3-(4-cyanophenyl)-1-oxo-1,2,3,4-tetrahydroisoquinolin-7-yl]-3-[4-(methylthio)phenyl]urea;
(R)-1-[2-(3-aminopropyl)-3-(4-cyanophenyl)-1-oxo-1,2,3,4-tetrahydroisoquinolin-7-yl]-3-[4-(methylthio)phenyl]urea;
(S)-1-[2-(3-aminopropyl)-3-(4-cyanophenyl)-1-oxo-1,2,3,4-tetrahydroisoquinolin-7-yl]-3-[4-(methylsulfinyl)phenyl]urea;
(S)-1-[2-(3-aminopropyl)-3-(4-cyanophenyl)-1-oxo-1,2,3,4-tetrahydroisoquinolin-7-yl]-3-[4-(methylsulfinyl)phenyl]urea;
(S)-1-[2-(3-aminopropyl)-3-(4-cyanophenyl)-1-oxo-1,2,3,4-tetrahydroisoquinolin-7-yl]-3-[4-(methylsulfonyl)phenyl]urea;
(R)-1-[2-(3-aminopropyl)-3-(4-cyanophenyl)-1-oxo-1,2,3,4-tetrahydroisoquinolin-7-yl]-3-[4-(methylsulfonyl)phenyl]urea;
1-[2-(3-aminopropyl)-3-methyl-1-oxo-1,2,3,4-tetrahydroisoquinolin-7-yl]-3-[4-(methylthio)phenyl]urea; and
1-[2-(3-aminopropyl)-3-methyl-1-oxo-1,2,3,4-tetrahydroisoquinolin-7-yl]-3-[4-(methylsulfonyl)phenyl]urea.

12. A pharmaceutical composition comprising as active ingredient a therapeutically effective amount of a compound according to claim 1 and a pharmaceutically acceptable adjuvant, diluents or carrier.

13. A pharmaceutical composition according to claim 12 wherein the compound is selected from:
1-(4-acetylphenyl)-3-[2-(3-aminopropyl)-3-(4-cyanophenyl)-1-oxo-1,2,3,4-tetrahydroisoquinolin-7-yl]urea;
1-(4-acetylphenyl)-3-[2-(2-aminoethyl)-3-(4-cyanophenyl)-1-oxo-1,2,3,4-tetrahydroisoquinolin-7-yl]urea;
1-(4-acetylphenyl)-3-{3-(4-cyanophenyl)-2-[2-(1H-imidazol-4-yl)ethyl]-1-oxo-1,2,3,4-tetrahydroisoquinolin-7-yl}urea;
1-(4-acetylphenyl)-3-{3-(4-cyanophenyl)-2-[2-(methylamino)ethyl]-1-oxo-1,2,3,4-tetrahydroisoquinolin-7-yl}urea;
1-[2-(3-aminopropyl)-3-(4-cyanophenyl)-1-oxo-1,2,3,4-tetrahydroisoquinolin-7-yl]-3-[4-(trifluoromethyl)phenyl]urea;
1-{3-(4-cyanophenyl)-2-[2-(1H-imidazol-4-yl)ethyl]-1-oxo-1,2,3,4-tetrahydroisoquinolin-7-yl}-3-[4-(trifluoromethyl)phenyl]urea;
1-[2-(3-aminopropyl)-3-(4-cyanophenyl)-1-oxo-1,2,3,4-tetrahydroisoquinolin-7-yl]-3-[4-(methylthio)phenyl]urea;
1-(4-acetylphenyl)-3-{3-(3,4-dichlorophenyl)-2-[2-(1H-imidazol-4-yl)ethyl]-1-oxo-1,2,3,4-tetrahydroisoquinolin-7-yl}urea;
1-[2-(3-aminopropyl)-3-(4-cyanophenyl)-1-oxo-1,2,3,4-tetrahydroisoquinolin-7-yl]-3-(4-bromophenyl)urea;
1-[2-(3-aminopropyl)-3-(4-cyanophenyl)-1-oxo-1,2,3,4-tetrahydroisoquinolin-7-yl]-3-[4-(methylsulfinyl)phenyl]urea;
1-[2-(3-aminopropyl)-3-(4-cyanophenyl)-1-oxo-1,2,3,4-tetrahydroisoquinolin-7-yl]-3-[4-(methylsulfonyl)phenyl]urea;

1-{3-(4-cyanophenyl)-2-[2-(1H-imidazol-4-yl)ethyl]-1-oxo-1,2,3,4-tetrahydroisoquinolin-7-yl}-3-[4-(methylthio)phenyl]urea;

1-{3-(4-cyanophenyl)-2-[2-(1H-imidazol-4-yl)ethyl]-1-oxo-1,2,3,4-tetrahydroisoquinolin-7-yl}-3-[4-(methylsulfinyl)phenyl]urea;

1-{3-(4-cyanophenyl)-2-[2-(1H-imidazol-4-yl)ethyl]-1-oxo-1,2,3,4-tetrahydroisoquinolin-7-yl}-3-[4-(methylsulfonyl)phenyl]urea;

1-{3-(6-fluoropyridin-3-yl)-2-[2-(1H-imidazol-4-yl)ethyl]-1-oxo-1,2,3,4-tetrahydroisoquinolin-7-yl}-3-[4-(methylthio)phenyl]urea;

1-{3-(5-fluoropyridin-2-yl)-2-[2-(1H-imidazol-4-yl)ethyl]-1-oxo-1,2,3,4-tetrahydro isoquinolin-7-yl}-3-[4-(methylsulfinyl)phenyl]urea;

1-{3-(5-fluoropyridin-2-yl)-2-[2-(1H-imidazol-4-yl)ethyl]-1-oxo-1,2,3,4-tetrahydro isoquinolin-7-yl}-3-[4-(methylsulfonyl)phenyl]urea;

1-{3-(2-furyl)-2-[2-(1H-imidazol-4-yl)ethyl]-1-oxo-1,2,3,4-tetrahydroisoquinolin-7-yl}-3-[4-(methylthio)phenyl]urea;

1-{3-(5-chloro-2-furyl)-2-[2-(1H-imidazol-4-yl)ethyl]-1-oxo-1,2,3,4-tetrahydroisoquinolin-7-yl}-3-[4-(methylthio)phenyl]urea;

1-(4-acetylphenyl)-3-{3-(6-chloropyridin-3-yl)-2-[2-(1H-imidazol-4-yl)ethyl]-1-oxo-1,2,3,4-tetrahydroisoquinolin-7-yl}urea;

1-{3-(6-chloropyridin-3-yl)-2-[2-(1H-imidazol-4-yl)ethyl]-1-oxo-1,2,3,4-tetrahydroisoquinolin-7-yl}-3-[4-(methylthio)phenyl]urea;

1-(4-acetylphenyl)-3-{3-(5-chloropyridin-2-yl)-2-[2-(1H-imidazol-4-yl)ethyl]-1-oxo-1,2,3,4-tetrahydroisoquinolin-7-yl}urea;

1-{3-(5-chloropyridin-2-yl)-2-[2-(1H-imidazol-4-yl)ethyl]-1-oxo-1,2,3,4-tetrahydro isoquinolin-7-yl}-3-[4-(methylthio)phenyl]urea;

1-{3-(5-chloropyridin-2-yl)-2-[2-(1H-imidazol-4-yl)ethyl]-1-oxo-1,2,3,4-tetrahydro isoquinolin-7-yl}-3-[4-(methylsulfonyl)phenyl]urea;

1-[2-(3-aminopropyl)-3-(4-cyanophenyl)-1-oxo-1,2,3,4-tetrahydroisoquinolin-7-yl]-3-[4-(ethylthio)phenyl]urea;

(S)-1-[2-(3-aminopropyl)-3-(4-cyanophenyl)-1-oxo-1,2,3,4-tetrahydroisoquinolin-7-yl]-3-[4-(methylthio)phenyl]urea;

(R)-1-[2-(3-aminopropyl)-3-(4-cyanophenyl)-1-oxo-1,2,3,4-tetrahydroisoquinolin-7-yl]-3-[4-(methylthio)phenyl]urea;

(S)-1-[2-(3-aminopropyl)-3-(4-cyanophenyl)-1-oxo-1,2,3,4-tetrahydroisoquinolin-7-yl]-3-[4-(methylsulfinyl)phenyl]urea;

(S)-1-[2-(3-aminopropyl)-3-(4-cyanophenyl)-1-oxo-1,2,3,4-tetrahydroisoquinolin-7-yl]-3-[4-(methylsulfinyl)phenyl]urea;

(S)-1-[2-(3-aminopropyl)-3-(4-cyanophenyl)-1-oxo-1,2,3,4-tetrahydroisoquinolin-7-yl]-3-[4-(methylsulfonyl)phenyl]urea;

(R)-1-[2-(3-aminopropyl)-3-(4-cyanophenyl)-1-oxo-1,2,3,4-tetrahydroisoquinolin-7-yl]-3-[4-(methylsulfonyl)phenyl]urea;

1-[2-(3-aminopropyl)-3-methyl-1-oxo-1,2,3,4-tetrahydroisoquinolin-7-yl]-3-[4-(methylthio)phenyl]urea; and 1-[2-(3-aminopropyl)-3-methyl-1-oxo-1,2,3,4-tetrahydroisoquinolin-7-yl]-3-[4-(methylsulfonyl)phenyl]urea.

* * * * *